United States Patent
Hong et al.

(10) Patent No.: US 12,042,629 B2
(45) Date of Patent: Jul. 23, 2024

(54) BIO-ELECTROCEUTICAL DEVICE USING CELL CLUSTER

(71) Applicant: SAMSUNG ELECTRONICS CO., LTD., Suwon-si (KR)

(72) Inventors: Young Jun Hong, Seoul (KR); Hyejin Park, Suwon-si (KR); Seokyung Kang, Seoul (KR); Soyoung Bang, Incheon (KR); Sang Joon Kim, Hwaseong-si (KR); Chisung Bae, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 927 days.

(21) Appl. No.: 17/092,661

(22) Filed: Nov. 9, 2020

(65) Prior Publication Data

US 2021/0220558 A1    Jul. 22, 2021

(30) Foreign Application Priority Data

Jan. 16, 2020    (KR) .................. 10-2020-0005729

(51) Int. Cl.
*A61M 5/172* (2006.01)
*A61B 5/145* (2006.01)
(Continued)

(52) U.S. Cl.
CPC ....... *A61M 5/1723* (2013.01); *A61B 5/14532* (2013.01); *A61B 5/1473* (2013.01);
(Continued)

(58) Field of Classification Search
CPC ........ A61M 5/1723; A61M 2005/1726; A61M 2202/07; A61M 2205/054; A61M 2230/201; A61M 5/14276; A61B 5/14532; A61B 5/1473; A61B 5/14865; A61B 5/4866; A61K 9/0009; A61K 38/28; A61K 35/39; C12M 35/02; A61F 2/022; C12N 5/0676

See application file for complete search history.

(56) References Cited

U.S. PATENT DOCUMENTS

| 5,919,216 A | 7/1999 | Houben et al. |
| 6,197,575 B1 | 3/2001 | Griffith et al. |

(Continued)

FOREIGN PATENT DOCUMENTS

| EP | 0 862 391 B1 | 8/2005 |
| JP | 2003-509098 A | 3/2003 |

(Continued)

OTHER PUBLICATIONS

Extended European Search Report issued on Jul. 6, 2021 in counterpart European Patent Application No. 20217401.7 (6 pages in English).

(Continued)

*Primary Examiner* — Theodore J Stigell
*Assistant Examiner* — Rachel T. Smith
(74) *Attorney, Agent, or Firm* — NSIP Law

(57) ABSTRACT

A bio-electroceutical device includes: a cell reservoir configured to accommodate a cell cluster comprising an organoid fused with a biomaterial; and a cell controller configured to control, using an electrical signal, a secretion of an active component by the organoid in the cell cluster.

22 Claims, 16 Drawing Sheets

(51) Int. Cl.
*A61B 5/1473* (2006.01)
*A61K 9/00* (2006.01)
*A61K 38/28* (2006.01)

(52) U.S. Cl.
CPC ............ *A61K 9/0009* (2013.01); *A61K 38/28* (2013.01); *A61M 2005/1726* (2013.01); *A61M 2202/07* (2013.01); *A61M 2205/054* (2013.01); *A61M 2230/201* (2013.01)

(56) References Cited

U.S. PATENT DOCUMENTS

| | | | |
|---|---|---|---|
| 8,348,886 | B2 | 1/2013 | Kanderian, Jr. et al. |
| 9,962,113 | B2 | 5/2018 | Lang et al. |
| 2004/0133188 | A1 | 7/2004 | Vardi et al. |
| 2005/0090607 | A1* | 4/2005 | Tapsak .................. C08L 83/12 524/588 |
| 2007/0037281 | A1 | 2/2007 | Kruse |
| 2015/0253309 | A1 | 9/2015 | Marx |
| 2022/0314212 | A1* | 10/2022 | Nielsen ............. G01N 15/1031 |
| 2022/0409773 | A1* | 12/2022 | Shimoda ............. A61K 9/0024 |

FOREIGN PATENT DOCUMENTS

| | | |
|---|---|---|
| JP | 2011-528653 A | 11/2011 |
| JP | 2013-532484 A | 8/2013 |
| JP | 2018-531027 A | 10/2018 |
| KR | 10-2012-0120299 A | 11/2012 |
| KR | 10-2018-0055683 A | 5/2018 |
| WO | WO 00/53257 A1 | 9/2000 |
| WO | WO-0053257 A1 * | 9/2000 ......... A61B 5/14532 |
| WO | WO 2019/106438 A1 | 6/2019 |
| WO | WO 2019/126626 A1 | 6/2019 |

OTHER PUBLICATIONS

Rafael, E., et al. "Longitudinal Studies on the Microcirculation Around the Theracyte™ Immunoisolation Device, Using the Laser Doppler Technique." Cell transplantation 9.1 (2000): (pp. 107-113).
Ma, Zhen, et al. "Self-organizing human cardiac microchambers mediated by geometric confinement." *Nature communications*, 6.1 (2015)(pp. 1-10).
Long, Yin, et al., "Effective Wound Healing Enabled by Discrete Alternative Electric Fields from Wearable Nanogenerators." ACS nano, 12.12, 2018 (pp. 12533-12540).
Jung, Chorok., "Organoids-Based Biomimetics", *Korea Research Institute of Bioscience and Biotechnology*, vol. 51, 2018 (14 pages in English and 10 pages in Korean).
"PEC-Encap™ (VC-01™)—Improving Diabetes Treatment", Viacyte, Inc., Jun. 23, 2019 (4 pages in English).
Oliveira, K. M. C., et al., "Electrical stimulation shifts healing/ scarring towards regeneration in a rat limb amputation model." *Scientific reports*, 9.1 (2019)(pp. 1-14).
Yu, Chao, et al., "A novel microcurrent dressing for wound healing in a rat skin defect model." *Military Medical Research*, 6.1 (2019): 22 (9 pages in English).

* cited by examiner

BIO-ELECTROCEUTICAL DEVICE USING CELL CLUSTER

CROSS-REFERENCE TO RELATED APPLICATIONS

This application claims the benefit under 35 USC § 119(a) of Korean Patent Application No. 10-2020-0005729, filed on Jan. 16, 2020, in the Korean Intellectual Property Office, the entire disclosure of which is incorporated herein by reference for all purposes.

BACKGROUND

1. Field

The following description relates to a bio-electroceutical device using cell clusters.

2. Description of Related Art

An artificial pancreas may be an artificial organ produced for the purpose of treating diabetes and may function as islets of Langerhans in a pancreas. For example, islets of Langerhans of animals of the same or different species may be sealed in a semipermeable membrane for preventing an immune rejection response and may be implanted in vivo.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a bio-electroceutical device includes: a cell reservoir configured to accommodate a cell cluster comprising an organoid fused with a biomaterial; and a cell controller configured to control, using an electrical signal, a secretion of an active component by the organoid in the cell cluster.

The cell cluster may be accommodated in the cell reservoir, and the cell cluster may include a hydrogel and a beta cell organoid disposed in the hydrogel.

The device may include: an electrochemical sensor configured to sense a target molecule, wherein, for the control of the secretion, the cell controller may be configured to adjust an active component generation rate of the organoid in the cell cluster based on a result of the sensing of the target molecule.

To sense the target molecule, the electrochemical sensor may be configured to sense another electrical signal generated by a reaction between the target molecule and an enzyme.

For the control of the secretion, the cell controller may be configured to perform either one or both of: applying an electrical stimulation that facilitates the secretion of the active component by the organoid in the cell cluster; and interrupting the electrical stimulation based on a concentration of the sensed target molecule.

The interrupt of the electrical stimulation may include either one or both of reduction of a level of the electrical stimulation and termination of the application of the electrical stimulation.

For the control of the secretion, the cell controller may be configured to: identify a metabolic state of a body based on a concentration of the sensed target molecule; and determine whether to apply an electrical stimulation to the cell cluster based on the identified metabolic state.

To sense the target molecule, the electrochemical sensor may be configured to sense a changed concentration of the target molecule, in response to the active component being secreted by the organoid in the cell cluster with the adjusted active component generation rate based on the electrical stimulation, and for the control of the secretion, the cell controller may be configured to reidentify the metabolic state based on the changed concentration and to redetermine whether to apply the electrical stimulation to the cell cluster based on the reidentified metabolic state.

For the control of the secretion, the cell controller may be configured to: apply, to the cell cluster, an electrical stimulation that facilitates the secretion of the active component by the organoid in the cell cluster, in response to a concentration level of the sensed target molecule being within a first range; and interrupt the electrical stimulation to the cell cluster, in response to the concentration level of the sensed target molecule being within a second range.

The electrochemical sensor may be configured to sense a blood glucose level of a body, and for the control of the secretion, the cell controller may be configured to apply, to the cell cluster, an electrical stimulation that facilitates a secretion of insulin by the organoid in the cell cluster, in response to the sensed blood glucose level exceeding a threshold level.

The active component may include insulin and the target molecule may include blood glucose.

For the control of the secretion, the cell controller may be configured to: determine a target generation rate for the active component generation rate based on the result of sensing the target molecule; and determine any one or any combination of a pulse width, a magnitude, a frequency, a phase and a waveform of the electrical signal, wherein the electrical signal is applied to the cell cluster based on the determined target generation rate.

For the control of the secretion, the cell controller may be configured to: determine a frequency of the electrical signal to be within any one of a beta frequency band, a gamma frequency band including 40 hertz (Hz), and a spike frequency band exceeding 400 Hz, and apply the electrical signal to the cell cluster.

The device may include: a control channel electrode configured to apply the electrical signal to the cell cluster; an active component channel electrode disposed between the cell cluster and a blood vessel; and a body channel electrode configured to apply another electrical signal to the blood vessel.

The cell controller may be configured to facilitate a regeneration of a capillary adjacent to the bio-electroceutical device using an active component channel electrode and a body channel electrode, in response to the bio-electroceutical device being in an implantation mode.

For the control of the secretion, the cell controller may be configured to facilitate the secretion of the active component by the organoid in the cell cluster by applying the electrical signal to the cell cluster using a control channel electrode, in response to the bio-electroceutical device being in a treatment mode.

The active component may be discharged to an outside of the bio-electroceutical device and combined with an ion transporter, and the cell controller may be configured to induce a movement of the active component to a blood vessel by applying another electrical signal to the outside of the bio-electroceutical device using an active component channel electrode, in response to the bio-electroceutical device being in a treatment mode.

To apply the other electrical signal to the outside of the bio-electroceutical device, the cell controller may be configured to form an electric path between the blood vessel and the active component channel electrode by applying either one of a direct current (DC) stimulation and an alternating current (AC) stimulation to the active component channel electrode.

The cell reservoir may be configured to be detached from the cell controller.

The cell reservoir may include a loading port configured to receive an injection of an additional cell cluster from an outside of the bio-electroceutical device.

The cell reservoir may be configured to accommodate an electrochemical sensor and may include an electrode disposed at an exterior of the cell reservoir to be electrically connected to the cell controller.

In another general aspect, a bio-electroceutical device includes: an electrochemical sensor configured to sense a target molecule in a body; a cell reservoir configured to accommodate a cell cluster comprising an organoid disposed in a biomaterial; and a cell controller configured to apply, to the cell cluster, an electrical signal that induces a secretion of an active component by the organoid, based on a result of the sensing of the target molecule.

In another general aspect, a processor-implemented method of a bio-electroceutical device includes: sensing, using an electrochemical sensor, a concentration level of target molecule disposed in a cell reservoir; determining a target generation rate of an active component secreted by an organoid disposed in a cell reservoir, based on the concentration level; determining an electrical signal to be applied to the organoid based on the target generation rate; and applying the electrical signal to the organoid to induce a secretion of the active component at the target generation rate.

A non-transitory computer-readable storage medium may store instructions that, when executed by a processor, configure the processor to perform the method.

Other features and aspects will be apparent from the following detailed description, the drawings, and the claims.

Figure 1:
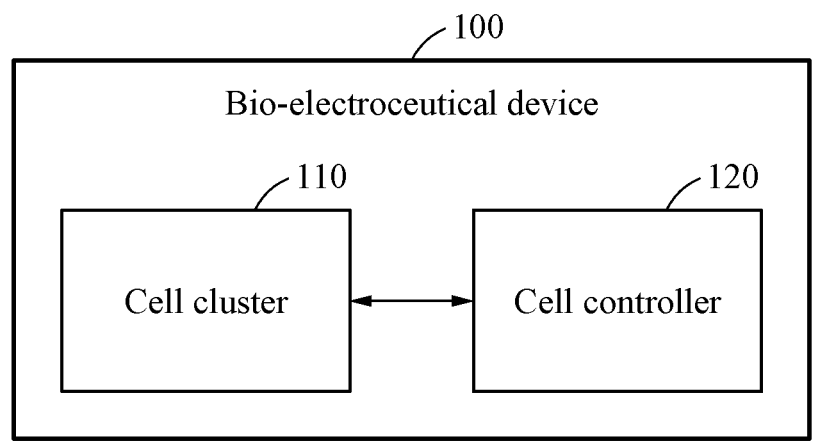
FIG. 1 illustrates an example of a bio-electroceutical device.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The terminology used herein is for the purpose of describing particular examples only, and is not to be used to limit the disclosure. As used herein, the singular forms "a," "an," and "the" are intended to include the plural forms as well, unless the context clearly indicates otherwise. As used herein, the term "and/or" includes any one and any combination of any two or more of the associated listed items. As used herein, the terms "include," "comprise," and "have" specify the presence of stated features, numbers, operations, elements, components, and/or combinations thereof, but do not preclude the presence or addition of one or more other features, numbers, operations, elements, components, and/or combinations thereof.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween. Likewise, expressions, for example, "between" and "immediately between" and "adjacent to" and "immediately adjacent to" may also be construed as described in the foregoing.

Unless otherwise defined, all terms, including technical and scientific terms, used herein have the same meaning as commonly understood by one of ordinary skill in the art to which this disclosure pertains consistent with and after an understanding of the present disclosure. Terms, such as those defined in commonly used dictionaries, are to be interpreted as having a meaning that is consistent with their meaning in the context of the relevant art and the present disclosure, and are not to be interpreted in an idealized or overly formal sense unless expressly so defined herein. The use of the term "may" herein with respect to an example or embodiment (e.g., as to what an example or embodiment may include or implement) means that at least one example or embodiment exists where such a feature is included or implemented, while all examples are not limited thereto.

Hereinafter, examples will be described in detail with reference to the accompanying drawings. The following specific structural or functional descriptions merely describe the examples, and the scope of the examples is not limited to the descriptions provided in the present specification. Like reference numerals in the drawings denote like elements, and a function or configuration known to one of ordinary skill in the art after an understanding of the present disclosure may be omitted herein.

Various modifications may be made to the examples. Here, the examples are not construed as limited to the disclosure and should be understood to include all changes, equivalents, and replacements within the idea and the technical scope of the disclosure.

When describing the examples with reference to the accompanying drawings, like reference numerals refer to like constituent elements and a repeated description related thereto will be omitted. In the description of examples, detailed description of related structures or functions will be omitted when it is deemed that such description will cause ambiguous interpretation of the present disclosure.

FIG. 1 illustrates an example of a bio-electroceutical device 100.

Referring to FIG. 1, the bio-electroceutical device 100 may include a cell cluster 110 and a cell controller 120.

The cell cluster 110 may include an organoid trapped in a biomaterial and may correspond to a fusion of the organoid and the biomaterial. An organoid may be a three-dimensional (3D) structure of cells capable of generating active components and may be a set of cells cultured and differentiated from stem cells in an in-vitro environment. For example, the organoid may be represented as an aggresome or a spheroid.

An active component may refer to a material with a pharmacological activity that has an influence on diagnosis, treatment, alleviation, cure, or prevention of diseases, or physiological functions of a human body. In the following description, the active component may be a material with a pharmacological activity that has an influence on physiological functions of a human body, and the active component may be insulin. Insulin may be a material that treats, alleviates, cures, or prevents diabetes. However, the active component is not limited to insulin, and the following description is also applicable to other active components.

When the bio-electroceutical device 100 is designed to secrete insulin as an active component, the cell cluster 110 may include a beta cell organoid trapped in a hydrogel that is a biomaterial. The beta cell organoid may be a mass of cells including at least one precursor corresponding to a last stage of a differentiation of pancreatic beta cells or a stage before the last stage. However, the cell cluster 110 including the beta cell organoid is not limited, and may further include other cells or materials. For example, the cell cluster 110 may include an alpha cell organoid together with the beta cell organoid. However, examples are not limited thereto, and the cell cluster 110 may further include a component for increasing an efficiency and a survival rate of each cell. Also, the cell cluster 110 may further include an additional factor for a stability of the organoid. The additional factor may be, for example, a culture medium.

In an example, the cell cluster 110 may mainly include an organoid of a predetermined cell. The cell cluster 110 may include a larger number of organoids of a predetermined cell than those of other cells. For example, the cell cluster 110 may include a beta cell organoid, or may include any one or any combination of an alpha cell organoid, a delta cell organoid and other pancreatic cells, together with the beta cell organoid. In this example, the cell cluster 110 may have a cell ratio different from that of islets of Langerhans. For example, a ratio of beta cell organoids with respect to organoids included in the cell cluster 110 may be greater than or equal to a threshold ratio. For example, a percentage of beta cell organoids in the cell cluster 110 may be greater than or equal to 85%. Examples are not limited thereto, and the percentage of beta cell organoids in the cell cluster 110 may be greater than or equal to 90%.

Also, the cell cluster 110 may be in an injectable form. When the biomaterial is a hydrogel, the cell cluster 110 in which the hydrogel and the organoid are fused may be injected through a flow path. Thus, the cell cluster 110 may be refilled by an injection, a non-limiting example of which will be described below with reference to FIG. 14.

The cell controller 120 may control a secretion of an active component by the organoid in the cell cluster 110 by applying an electrical signal to the cell cluster 110. For example, the cell controller 120 may control the cell cluster 110 through a sensing channel and a stimulation channel of a control channel. The cell controller 120 may facilitate a generation of an active component by the organoid in the cell cluster 110 by applying an electrical stimulation to the cell cluster 110 through an electrode of the stimulation channel. The cell controller 120 may obtain a result of sensing a target molecule by an electrochemical sensor through an electrode of the sensing channel and may adjust an active component generation rate of the organoid in the cell cluster 110 based on the result. Non-limiting examples of the electrochemical sensor will be described below with reference to FIGS. 2, 5A, 5B and 5C.

As described above, the cell controller 120 may use and determine information obtained by the electrochemical sensor through the sensing channel of the control channel, and controls the cell cluster 110 through the stimulation channel of the control channel. Thus, the bio-electroceutical device 100 may adjust an active component secretion amount based on an amount of a target molecule while operating as a closed-loop system. By adjusting the active component secretion amount, an amount of a target molecule in a body may also be adjusted.

Figure 2:
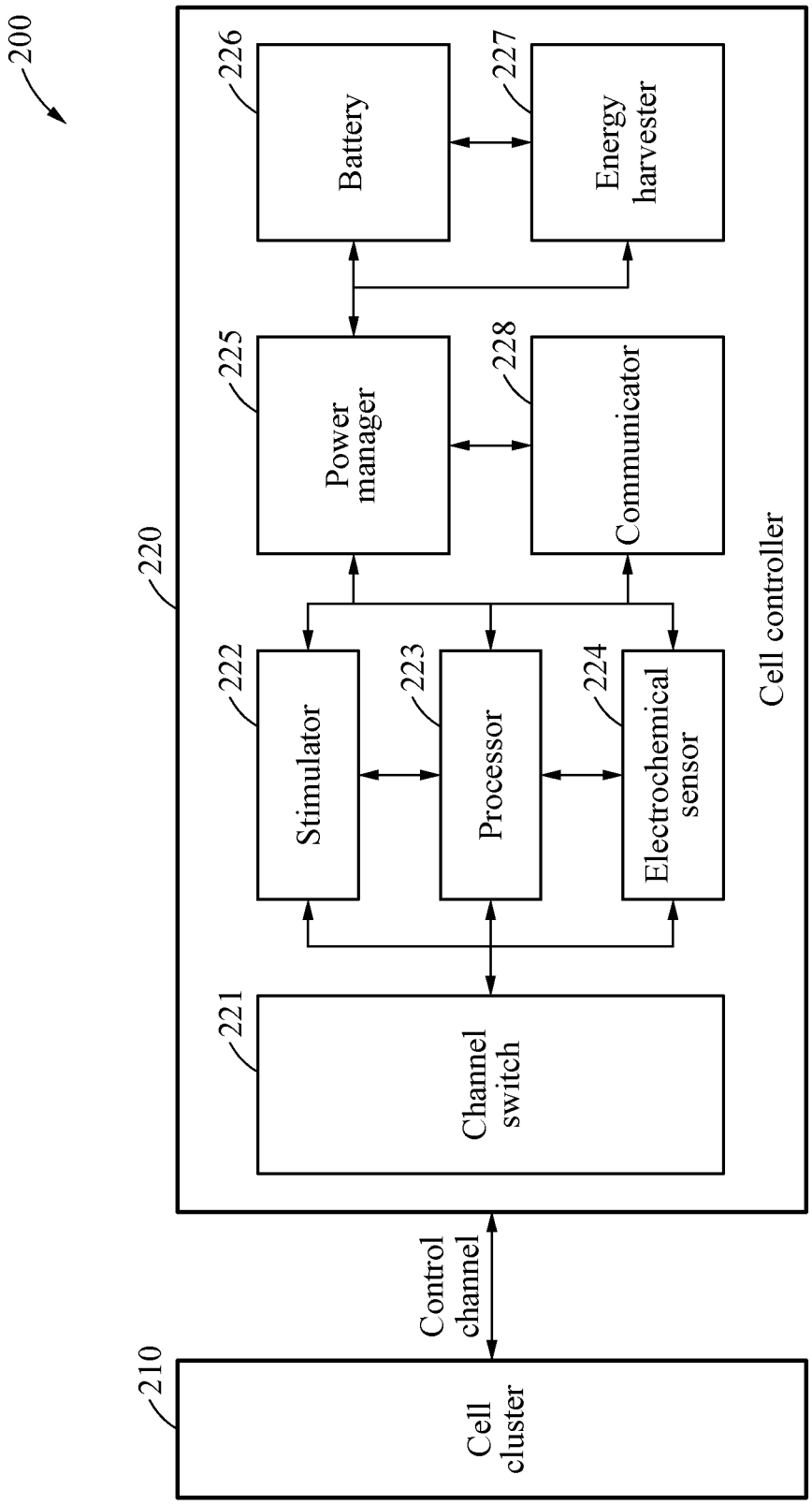
FIG. 2 illustrates an example of a bio-electroceutical device.

FIG. 2 illustrates an example of a bio-electroceutical device 200.

Referring to FIG. 2, a cell controller 220 may include a channel switch 221, a stimulator 222, a processor 223 (e.g., one or more processors), an electrochemical sensor 224, a power manager 225, a battery 226, an energy harvester 227, and a communicator 228.

The channel switch 221 may switch a connection to a channel electrode that applies and receives an electrical signal. The channel switch 221 may change a connection to electrodes (for example, a working electrode, a reference electrode, or a counter electrode) of a control channel that are electrically connected to, or disposed adjacent to, the cell cluster 210 for each operating mode when the stimulator 222 and the electrochemical sensor 224 are operating. In an example, the cell controller 220 may connect an electrode of a sensing channel to the electrochemical sensor 224 using the channel switch 221 to measure an amount of a target molecule. In another example, the cell controller 220 may connect an electrode of a stimulation channel to the stimulator 222 using the channel switch 221 to secrete an active component by an organoid in the cell cluster 210. However, channels including electrodes are not limited thereto.

The stimulator 222 may apply an electrical signal determined by the processor 223 to the electrode of the stimulation channel. For example, the stimulator 222 may apply an electrical signal with an amplitude, a magnitude, a frequency, a phase, and a waveform determined by the processor 223 to the stimulation channel. The electrode of the stimulation channel may be disposed adjacent to the cell cluster 210, for example, to provide an electrical signal to the cell cluster 210.

The electrochemical sensor 224 may electrochemically sense a target molecule. For example, the electrochemical sensor 224 may be or include a transducer, and the electrochemical sensor 224 may include a material (for example, an enzyme) that chemically reacts with the target molecule to generate electricity and may include an electrode to which the material is applied, that is in contact with the material, or that is connected to the material. However, the electrochemical sensor 224 is not limited thereto. In an example, the cell controller 220 may electrochemically monitor a concentration of a target molecule in a body using the electrochemical sensor 224. The electrochemical sensor 224 will be further described below with reference to FIGS. 5A, 5B and 5C, as non-limiting examples.

Figure 13:
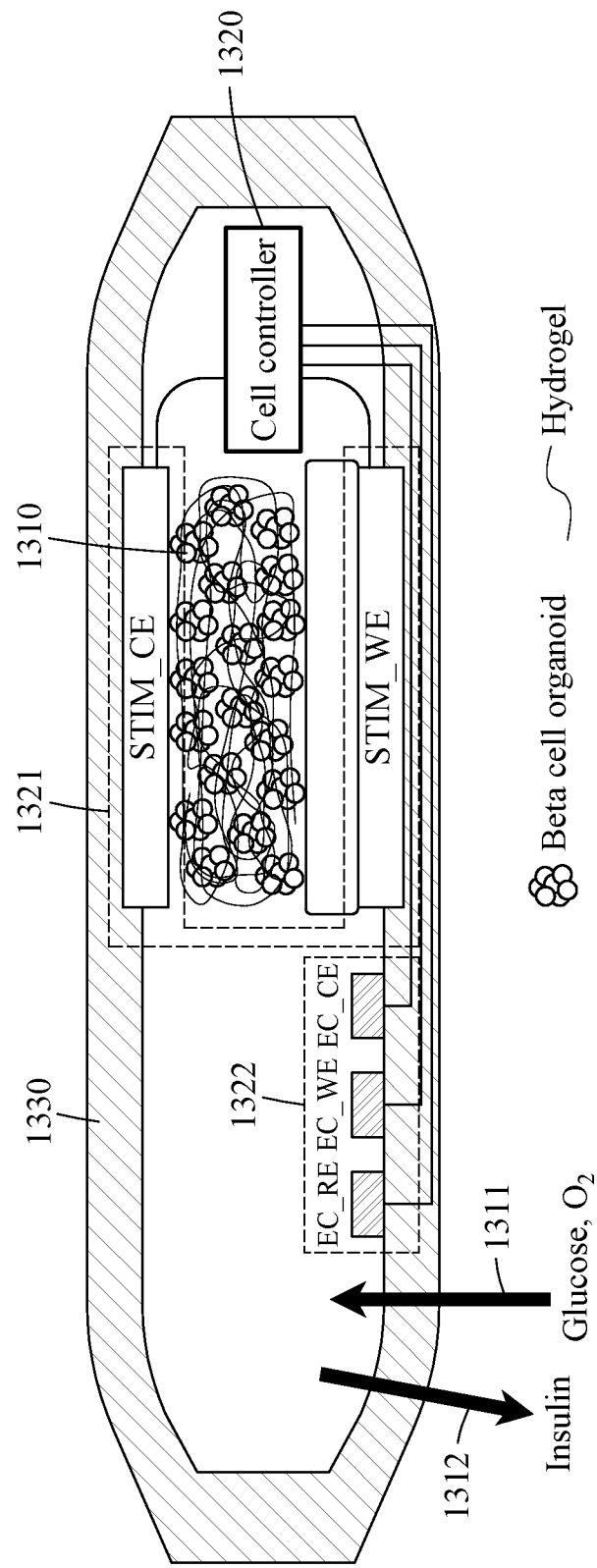
FIG. 13 illustrates an example of an application of a bio-electroceutical device.

The processor 223 may control the channel switch 221, the stimulator 222, the electrochemical sensor 224, and the power manager 225. Also, the processor 223 may identify a metabolic state of a body based on a sensing result of the target molecule and control an operation of each element based on the identified metabolic state. For example, the processor 223 may identify the metabolic state based on the concentration of the target molecule and may determine whether to apply an electrical stimulation to the cell cluster 210 based on the identified metabolic state. The metabolic state may be classified based on an amount, a concentration and/or a level of a target molecule contained in a body, and may include, for example, a state in which an input of an active component is required (e.g., a state in which the processor 223 may determine to input the active component) and a state in which an input of an active component is not required (e.g., a state in which the processor 223 may determine to exclude input of the active component). As shown in FIG. 13, a target molecule may be a blood glucose and a metabolic state of a body may be classified as, for example, a hyperglycemic state, a normal state, or a hypoglycemic state.

The power manager 225 may manage power of the cell controller 220. For example, the power manager 225 may charge the battery 226 with power generated by the energy harvester 227. The power manager 225 may operate other modules (for example, the channel switch 221, the stimulator 222, the processor 223, or the electrochemical sensor 224) using power stored in the battery 226. Also, the power manager 225 may operate the cell controller 220 using power generated by the energy harvester 227.

The battery 226 may store power to operate the cell controller 220.

The energy harvester 227 may generate power in response to an external signal. For example, the energy harvester 227 may generate power using a piezoelectric element in response to receiving a signal (for example, an ultrasonic signal or an electromagnetic wave signal) oscillating through a medium.

The communicator 228 may establish a wireless communication with an external device. For example, the communicator 228 may transmit a signal to the external device or receive a signal from the external device via the wireless communication. The communicator 228 may transmit information (for example, information associated with the concentration of the target molecule) collected by the bio-electroceutical device 200 and information (for example, a pulse of an electrical stimulation and a point in time of an electrical stimulation for drug secretion) associated with an operation of the bio-electroceutical device 200 to the external device. Also, the communicator 228 may receive a control signal for the bio-electroceutical device 200 from the external device. In an example, the processor 223 may control the channel switch 221, the stimulator 222, the electrochemical sensor 224, and/or the power manager 225 based on the received control signal.

Thus, the bio-electroceutical device 200 may enhance an efficacy of the cell cluster 210 and increase a therapeutic effect by activating a secretion of the active component by the organoid in the cell cluster 210 using the cell controller 220.

Figure 3:
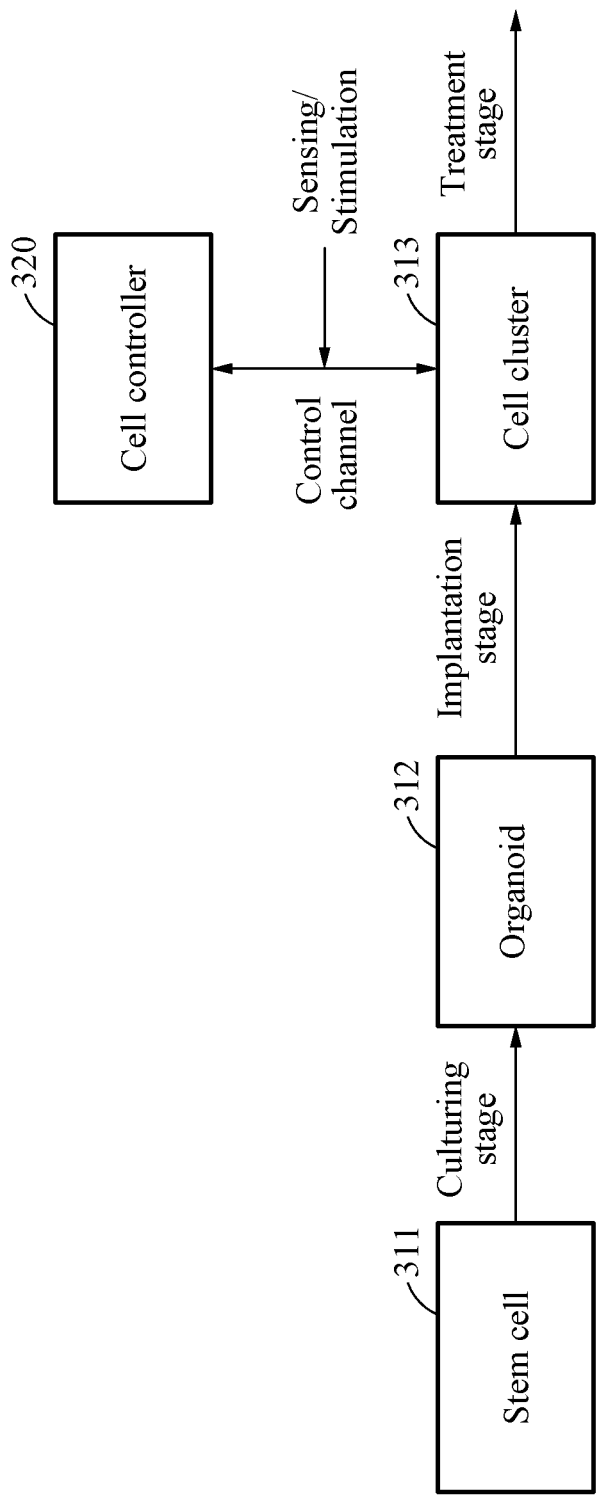
FIG. 3 illustrates an example of a culturing of a cell cluster of a bio-electroceutical device, an implantation of the bio-electroceutical device, and a treatment using the cell cluster.

FIG. 3 illustrates an example of an implantation of a bio-electroceutical device and a treatment using a cell cluster.

A cell cluster 313 may be a 3D structure in which an organoid 312 and a biomaterial are fused. An organoid may be a 3D cell aggregate including cells (for example, beta cells) specific for a model organ (for example, a pancreas). The organoid 312 may be differentiated from a stem cell 311 and may include, for example, a beta cell organoid.

The organoid 312 may correspond to a 3D cell mass having any one or any combination of a structure, cellular components, and functions similar to a living organ, and may function as an artificial organ when a biosimilarity increases by an implantation. For example, the cell cluster 313 may include the organoid 312 that is completely implanted. The beta cell organoid may be, for example, a cell aggregate including at least one beta cell precursor or at least one beta cell.

For example, to increase a cell survival rate, the cell cluster 313 may include an activation factor and a biomaterial fused with a cell aggregate. However, examples are not limited to the biomaterial and the activation factor, and the cell cluster 313 may include other materials for increasing a survival rate, a stability, and an effectiveness of the beta cell organoid.

A cell controller 320 may increase an active component secretion ability of the organoid in the cell cluster 313 using an electrochemical sensing and an electrical stimulation as described above. However, an operation of the cell controller 320 is not limited to a treatment mode and the cell controller 320 may also act on a survival of the cell cluster 313.

Figure 4:
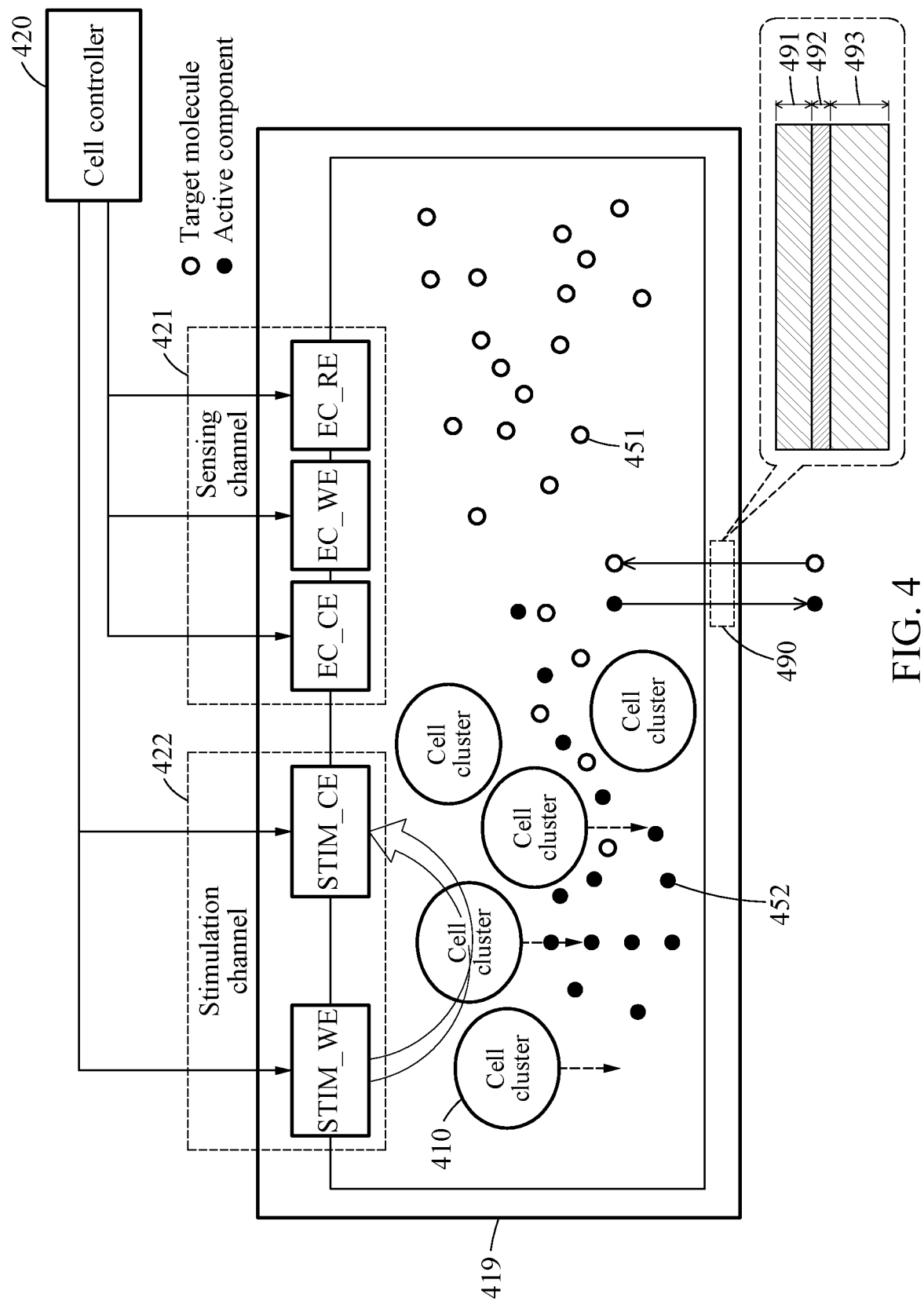
FIG. 4 illustrates an example of secreting an active component by an organoid in a cell cluster through an electrical stimulation in a bio-electroceutical device.

FIG. 4 illustrates an example of secreting an active component by an organoid in a cell cluster through an electrical stimulation in a bio-electroceutical device.

A cell controller 420 may adjust an active component generation rate of an organoid in a cell cluster 410 based on a result of sensing a target molecule 451. For example, the cell controller 420 may apply an electrical stimulation that facilitates a secretion of an active component by the organoid in the cell cluster 410 to the cell cluster 410 or may interrupt (e.g., cease or reduce) the electrical stimulation to the cell cluster 410, based on a concentration of the sensed target molecule 451.

As shown in FIG. 4, electrodes of a stimulation channel 422 (stimulation working electrode STIM_WE and stimulation counter electrode STIM_CE) and electrodes of a sensing channel 421 (sensing counter electrode ECCE, sensing working electrode EC_WE, and sensing reference electrode EC_RE) are connected to the cell controller 420. The above electrodes may be electrically connected to the cell cluster 410 and/or disposed adjacent to the cell cluster 410. For example, the electrodes STIM_WE and STIM_CE of the stimulation channel 422 and the electrodes ECCE, EC_WE and EC_RE of the sensing channel 421 may be disposed in a cell reservoir 419 that accommodates (e.g., contains or encloses) the cell cluster 410. Electrodes of the stimulation channel 422 and the sensing channel 421 may be isolated externally from the bio-electroceutical device or from other components of the bio-electroceutical device.

The cell controller 420 may sense the target molecule 451 introduced into the cell reservoir 419 using the electrodes of the sensing channel 421. An electrochemical sensor may sense an electrical signal caused by a chemical reaction between the target molecule 451 and an enzyme applied to the sensing working electrode EC_WE, non-limiting examples of which will be further described below with reference to FIGS. 5A through 5C. The cell controller 420 may determine the concentration of the target molecule 451 in the cell reservoir 419 based on a magnitude (for example, a voltage or a current) of an electrical signal caused by the chemical reaction. The concentration of the target molecule 451 in the cell reservoir 419 may correspond to, for example, a concentration of the target molecule 451 in a body.

The cell controller 420 may apply an electrical signal to the cell cluster 410 through the electrodes STIM_WE and STIM_CE of the stimulation channel 422. For example, the cell controller 420 may apply an electrical signal through an electrode channel from the stimulation working electrode STIM_WE via at least one cell cluster 410 to a stimulation counter electrode STIM_CE. An organoid in the cell cluster 410 stimulated by the electrical signal may secrete an active component 452. For example, in response to a stimulation, the organoid in the cell cluster 410 may secrete the active component 452 with a generation rate increased in comparison to before the stimulation. The active component 452 secreted by the organoid in the cell cluster 410 may be discharged from the cell reservoir 419.

In an example, the cell controller 420 may determine a target generation rate based on the result of sensing the target molecule 451 and may determine any one or any combination of a pulse width, a magnitude, a frequency, a phase, and a waveform of an electrical signal applied to the cell cluster 410 based on the determined target generation rate. Non-limiting examples of parameters of an electrical signal determined and controlled by the cell controller 420 will be further described below with reference to FIGS. 6 and 7. The electrodes STIM_WE and STIM_CE of the stimulation channel 422 may induce the secretion of the active component based on the target generation rate for the organoid in the cell cluster 410, by providing an electrical signal determined by the cell controller 420 to the cell cluster 410.

The cell reservoir 419 may be formed of a material through which the target molecule 451 and the active component 452 pass, and may be implemented as a structure that accommodates the cell cluster 410. For example, the cell reservoir 419 may include a porous membrane 490 that encloses and accommodates the cell cluster 410. The porous membrane 490 may be configured such that the target molecule 451 and the active component 452 pass through the porous membrane 490. The porous membrane 490 may include multiple layers. For example, the porous membrane 490 may include a first membrane layer 491, a second membrane layer 492, and a support fiber layer 493. The porous membrane 490 may enclose the entire outer edge of the cell reservoir 419, however, examples are not limited thereto. For example, the porous membrane 490 may cover a portion of the outer edge of the cell reservoir 419 and a nonporous cover may cover the remaining portions of the outer edge of the cell reservoir 419.

The first membrane layer 491 may prevent an immune cell in a body (e.g., an immune cell external to the cell reservoir 419) from penetrating into the cell reservoir 419. The first membrane layer 491 may be formed of polytetrafluoroethylene and may have a thickness of about 30 micrometer (μm) and pores with a diameter less than 0.5 μm. The second membrane layer 492 may be formed of polytetrafluoroethylene and may have a thickness of about 15 μm and pores with a diameter of about 5 μm. The support fiber layer 493 may be a layer that prevents a damage of internal elements (for example, a cell cluster or a cell controller) due to a physical external force such as a pressure in a body by supporting mechanical and physical structures, may be formed of polyester, and may have a thickness exceeding 150 μm and pores with a diameter exceeding 100 μm. A thickness of each layer is not limited to those described above and may vary depending on a design. The first membrane layer 491 may be disposed adjacent to a cell cluster in a cell reservoir, and the support fiber layer 493 may be disposed outside the cell reservoir 419 or as an outer wall of the cell reservoir 419. The second membrane layer 492 may be disposed between the first membrane layer 491 and the support fiber layer 493. Due to a structure of the above-described porous membrane 490, the active component 452 and the target molecule 451 may freely enter and exit the cell reservoir 419 and an immune cell may be blocked from entering the cell reservoir 419. For example, a diameter of each of the active component 452 and the target molecule 451 may be smaller than a diameter of each of the layers 491, 492, and 493, and a diameter of the immune cell may be greater than one or more of the layers 491, 492, and 493.

As described above, the active component 452 secreted by the organoid in the cell cluster 410 may be discharged from the cell reservoir 419 and thus injected into the body. The active component 452 injected into the body may act on the body, and accordingly a metabolic situation may be regulated and the concentration of the target molecule 451 may change. The bio-electroceutical device may reidentify a metabolic state of the body changed every time a secretion of an active component is facilitated by the cell controller 420 and/or a metabolic state of the body changed by metabolism at regular intervals.

For example, when the cell cluster 410 secretes the active component 452 with a changed active component generation rate in response to an electrical stimulation, an electrochemical sensor may sense a changed concentration of the target molecule 451. Thus, the bio-electroceutical device may apply an electrical stimulation signal to the cell cluster 410 and may monitor feedback based on a result obtained by secreting the active component 452 by the organoid in the cell cluster 410. The cell controller 420 may reidentify the metabolic state based on the changed concentration, and may redetermine whether to apply the electrical stimulation to the cell cluster 410 based on the reidentified metabolic state. Thus, the cell controller 420 may measure the concentration of the target molecule 451 in the body every time a secretion of an active component is facilitated and inhibited, and may determine whether a treatment is required (e.g., whether to again secrete the active component).

Figure 5A:
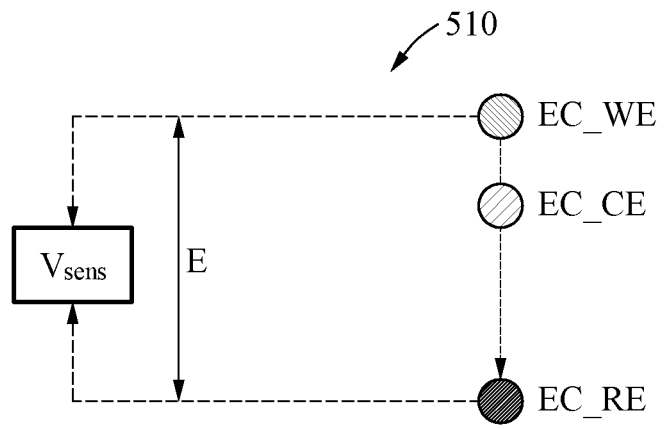
FIGS. 5A through 5C illustrate examples of an electrochemical sensor of a bio-electroceutical device.
Figure 5B:
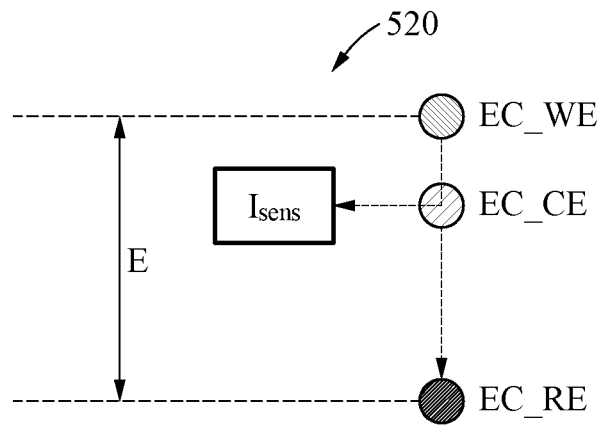
Figure 5C:
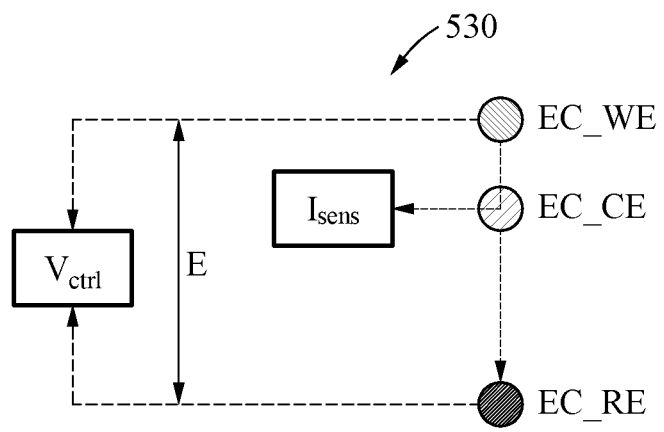

FIGS. 5A through 5C illustrate examples of an electrochemical sensor of a bio-electroceutical device.

The bio-electroceutical device may include an electrochemical sensor configured to sense a target molecule. FIGS. 5A through 5C respectively illustrate configurations of electrochemical sensors 510, 520, and 530. For example, an electrochemical sensor may sense an electrical signal generated by a reaction between a target molecule and an enzyme. The enzyme may be applied to a sensing working electrode EC_WE of a sensing channel, and the electrochemical sensor may sense, through the sensing working electrode EC_WE, an electrical signal (for example, a voltage and/or a current of the electrical signal) caused by a chemical reaction between the enzyme and the target molecule. For example, a potential voltage may change in a portion of the sensing working electrode EC_WE to which the enzyme is applied, in proportion to a blood glucose concentration, and the bio-electroceutical device may sense a blood glucose concentration in a body based on the potential voltage.

The electrochemical sensor 510 of FIG. 5A may measure a potential voltage using a potentiometry. For example, the electrochemical sensor 510 may sense a potential voltage between the sensing working electrode EC_WE and a sensing reference electrode EC_RE, without driving power. The electrochemical sensor 510 may be implemented by a molecularly imprinted polymer.

The electrochemical sensor 520 of FIG. 5B may measure a current using an amperometry. For example, the electrochemical sensor 520 may sense currents flowing from the sensing working electrode EC_WE to a sensing counter electrode ECCE, without driving power. The electrochemical sensor 520 may be implemented by a glucose oxidase enzyme (GOx).

The electrochemical sensor 530 of FIG. 5C may operate using a cyclic voltammetry (CV) or an electrochemical impedance spectroscopy (EIS). For example, the potential voltage between the sensing working electrode EC_WE and the sensing reference electrode EC_RE may be provided as driving power in the electrochemical sensor 530, and the electrochemical sensor 530 may sense currents flowing from the sensing working electrode EC_WE to the sensing counter electrode ECCE. The electrochemical sensor 530 may be implemented using a boronic acid.

Figure 6:
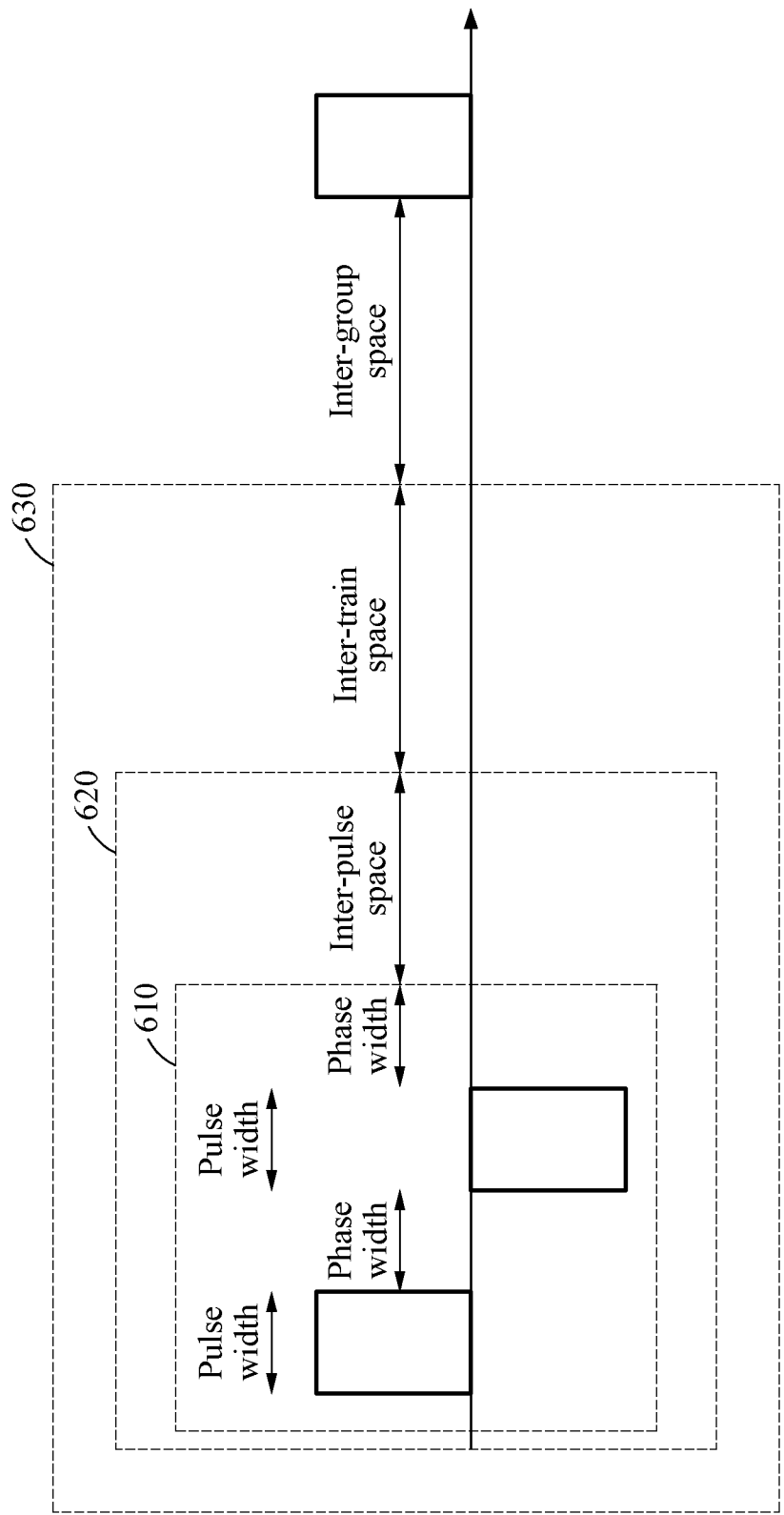
FIGS. 6 and 7 illustrate examples of an electrical stimulation applied to a cell cluster by a bio-electroceutical device.
Figure 7:
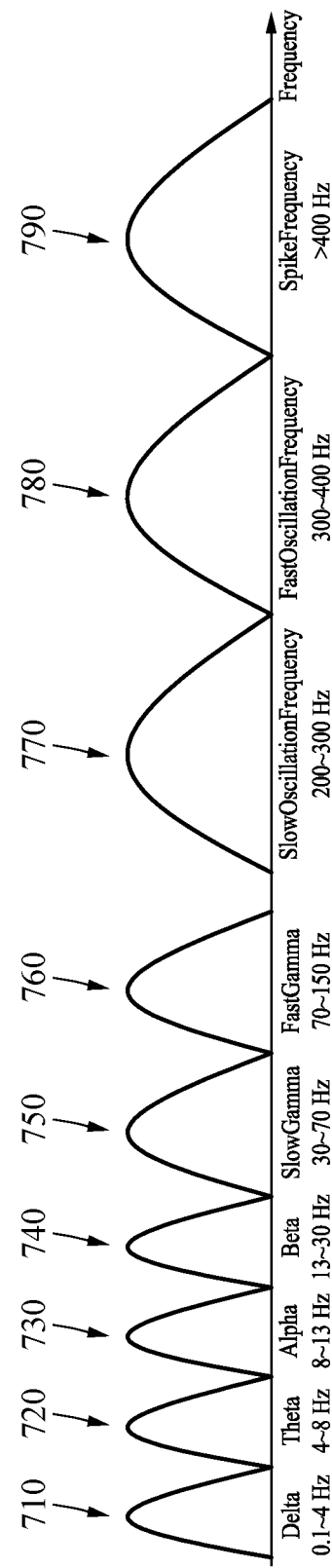

FIGS. 6 and 7 illustrate examples of an electrical stimulation applied to a cell cluster by a bio-electroceutical device.

FIG. 6 illustrates parameters of an electrical signal used for a stimulation of a cell cluster.

A cell controller may control a pulse width, a current intensity, a frequency of a pulse, a phase, and a waveform. The cell controller may determine and control parameters of an individual pulse 610, a pulse-train 620 that is a set of pulses, and a train group 630 that is a set of pulse-trains 620.

A pulse width is a width of an on period in the individual pulse 610. The on period is a period in which a positive electrical signal or a negative electrical signal is present. The positive electrical signal or the negative electrical signal indicates a sign of a signal applied to a working electrode. A phase width, an inter-pulse space, an inter-train space, and an inter-group space correspond to an off period, and the off period is a period in which an electrical signal is absent. Although the train group 630 includes a single pulse-train 620 and the pulse-train 620 includes a single pulse as shown in FIG. 6 for convenience of description, examples are not limited thereto. A number of pulses per pulse-train 620, a number of pulse-trains 620 per train group 630, and a number of groups may vary depending on settings and user' control.

When an electrical signal is applied for a relatively short period of time, the cell controller may apply a mono-phasic pulse to the cell cluster. The mono-phasic pulse may be a pulse with either a positive electrical signal or a negative electrical signal, but not both the positive electrical signal and the negative electrical signal.

The cell controller may apply a symmetric bi-phasic pulse to the cell cluster as shown in FIG. 6. A bi-phasic pulse may be a pulse having a positive electrical signal and a negative electrical signal that alternate. The bi-phasic pulse may preserve charge balancing in the cell cluster, and thus may be used for a long period of time in comparison to the mono-phasic pulse. The symmetric bi-phasic pulse may be a pulse in which an intensity and a pulse width of a positive pulse are respectively the same as an intensity and a pulse width of a negative pulse. However, examples are not limited to those of FIG. 6, and an asymmetric bi-phasic pulse may be applied to the cell cluster. The asymmetric bi-phasic pulse may be a pulse in which either one or both of an intensity and a pulse width of a positive pulse are respectively different from an intensity and a pulse width of a negative pulse. The individual pulse 610 may have a current intensity of 0 milliamperes (mA) to 8 mA, a pulse width of 5 microseconds (μs) to 2,000 μs, and a frequency of 0.1 hertz (Hz) to 40,000 Hz.

FIG. 7 illustrates pulse frequency bands controllable by a cell controller.

The cell controller may adjust a frequency of an electrical stimulation based on a bio-signal spectrum. As shown in FIG. 7, frequency bands controllable by the cell controller may be classified as a delta frequency band 710 of 0.1 Hz to 4 Hz, a theta frequency band 720 of 4 Hz to 8 Hz, an alpha frequency band 730 of 8 Hz to 13 Hz, a beta frequency band 740 of 13 Hz to 30 Hz, a slow gamma frequency band 750 of 30 Hz to 70 Hz, a fast gamma frequency band 760 of 70 Hz to 150 Hz, a slow oscillation frequency band 770 of 200 Hz to 300 Hz, a fast oscillation frequency band 780 of 300 Hz to 400 Hz, and a spike frequency band 790 exceeding 400 Hz.

The cell controller may facilitate a secretion of an active component by an organoid in a cell cluster using an electrical signal of pulses with frequencies in one or more of the above-described frequency bands 710 through 790. For example, the cell controller may determine a frequency of an electrical signal applied to the cell cluster within one of the beta frequency band 740, the slow gamma frequency band 750 including 40 Hz, the fast gamma frequency band 760, and the spike frequency band 790 exceeding 400 Hz.

For example, a beta organoid of a cell cluster may include an adrenergic receptor and the adrenergic receptor may respond to the alpha frequency band 730 and the beta frequency band 740. In an example, the cell controller may inhibit a secretion of an active component (for example, insulin) by applying an electrical signal with a frequency of the alpha frequency band 730. In another example, the cell controller may facilitate a secretion of insulin by applying an electrical signal with a frequency of the beta frequency band 740. However, examples are not limited thereto, and the cell controller may also facilitate a secretion of insulin by applying an electrical signal with a frequency of about 40 Hz to a cell cluster including a beta cell organoid.

Also, the cell controller may facilitate a secretion of an active component by an organoid in a cell cluster by applying an electrical signal with a frequency of the spike frequency band 790 to the cell cluster. For example, the cell controller may apply an electrical signal with a frequency of the spike frequency band 790, to activate a cell ion gate of the organoid in the cell cluster. Also, the cell controller may adjust a pulse width of an electrical stimulation, to activate the cell ion gate of the organoid in the cell cluster.

However, a frequency band of the cell controller is not limited to the above description. For example, to facilitate a secretion of an active component by an organoid in a cell cluster, the cell controller may apply a stimulation pulse with any of the other frequency bands.

Figure 8:
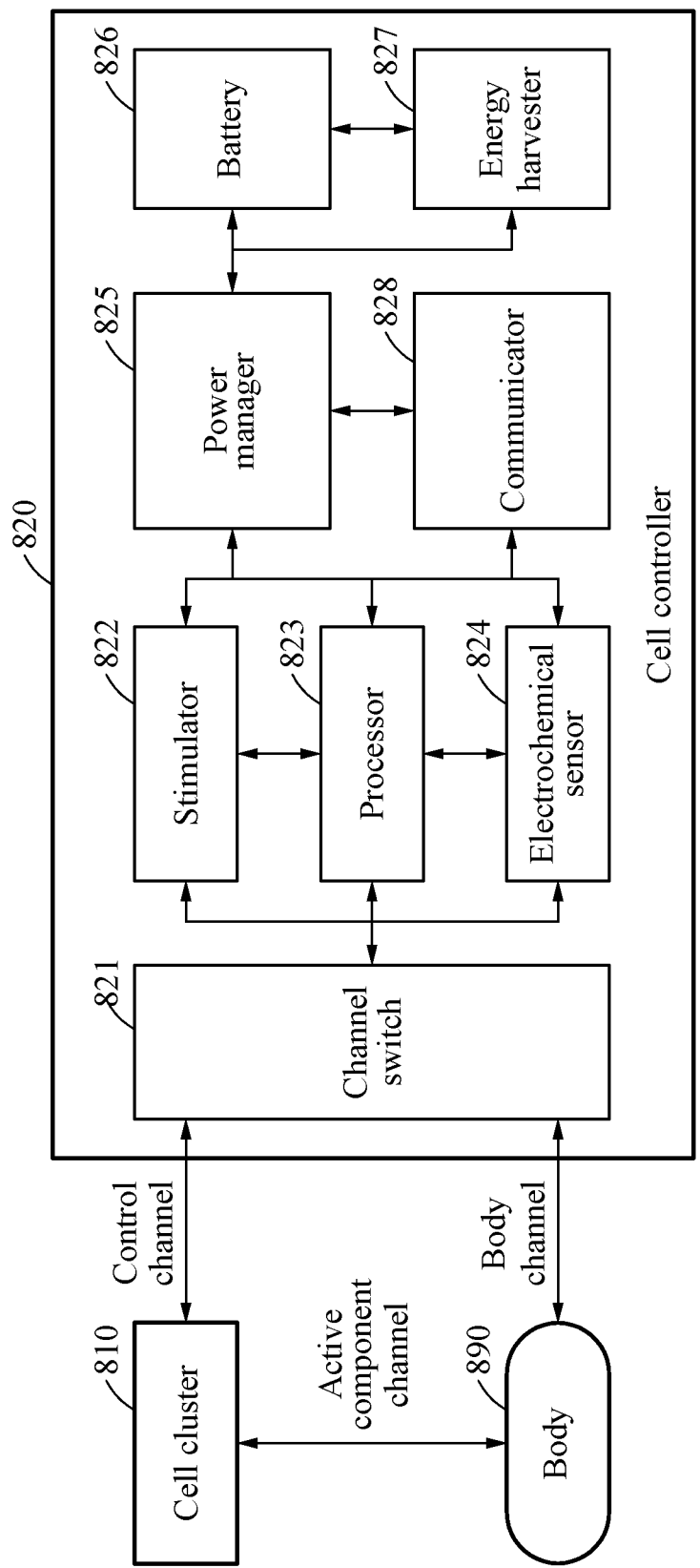
FIG. 8 illustrates an example of electrode channels of a bio-electroceutical device.

FIG. 8 illustrates an example of electrode channels of a bio-electroceutical device.

Referring to FIG. 8, a cell controller 820 may include a channel switch 821, a stimulator 822, a processor 823 (e.g., one or more processors), an electrochemical sensor 824, a power manager 825, a battery 826, an energy harvester 827, and a communicator 828. The stimulator 822, the electrochemical sensor 824, the power manager 825, the battery 826, the energy harvester 827 and the communicator 828 may operate similarly to those of FIG. 2, and thus further description thereof is not repeated herein.

The bio-electroceutical device may further include additional electrode channels in addition to a control channel for facilitating and inhibiting a secretion of an active component by an organoid in a cell cluster 810 as described above. For example, the control channel may be a channel between the cell cluster 810 and the cell controller 820, and a body channel may be a channel between a body 890 and the cell controller 820. An active component channel may be a channel between the cell cluster 810 and the body 890. The bio-electroceutical device may include a control channel electrode, a body channel electrode, and an active component channel electrode for individual channels.

The control channel electrode may be an electrode disposed to allow an electrical signal to be applied to the cell cluster 810, and may include a stimulation channel electrode and a sensing channel electrode such as described above (e.g., such as the electrode of the stimulation channel and the electrode of the sensing channel described above with reference to FIG. 2).

The active component channel electrode may be an electrode disposed between the cell cluster 810 and the body 890 (for example, a blood vessel), and may be associated with an implantation of the bio-electroceutical device and an absorption of an active component secreted by an organoid in the cell cluster 810.

The body channel electrode may be an electrode disposed to allow an electrical signal to be applied to the body 890 (for example, a blood vessel), and may be associated with the implantation of the bio-electroceutical device.

Figure 9:
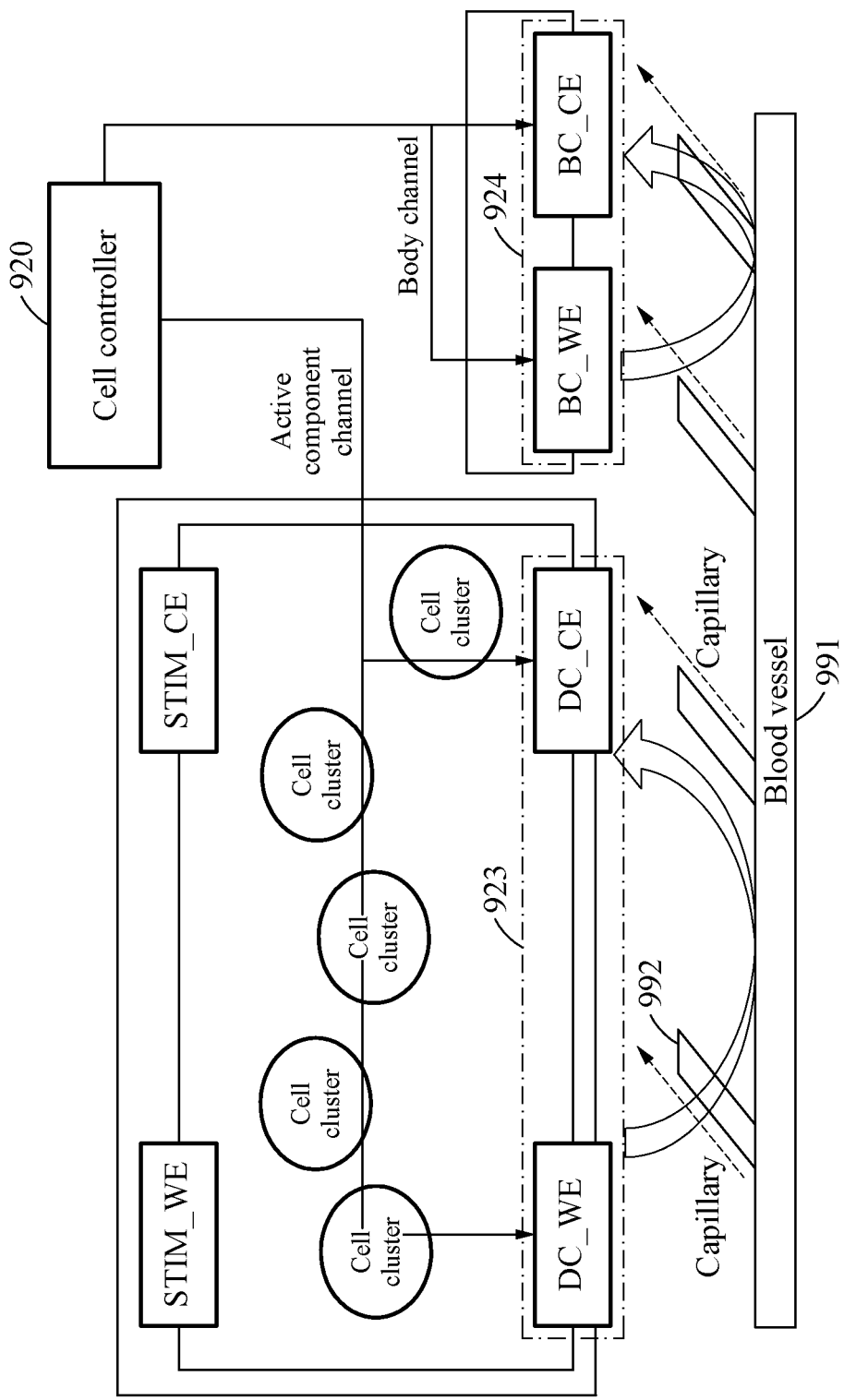
FIG. 9 illustrates an example of an implantation operation performed by a bio-electroceutical device.

FIG. 9 illustrates an example of an implantation operation performed by a bio-electroceutical device.

The bio-electroceutical device may perform an implantation operation of engrafting the bio-electroceutical device into a body. The bio-electroceutical device may be determined to be fully implanted and engrafted into the body after a predetermined amount of time. A cell controller 920 may perform a sensing operation and a stimulation operation to increase an engraftment rate of the bio-electroceutical device through an active component channel and a body channel in an in vivo environment. The cell controller 920 may enhance an active component acceptability through an electrical stimulation that induces a treatment of a region (for example, a blood vessel or a capillary) around a part of the body in which the bio-electroceutical device is inserted, through the active component channel and the body channel. By applying an electrical stimulation to a capillary 992 through the active component channel and the body channel, a regeneration of the capillary 992 may be facilitated to enhance the active component acceptability.

For example, in response to the bio-electroceutical device being in an implantation mode, the cell controller 920 may facilitate the regeneration of the capillary 992 adjacent to the bio-electroceutical device through an active component channel electrode and a body channel electrode. For example, the cell controller 920 may apply an electrical stimulation to a blood vessel 991 and the capillary 992 adjacent to the bio-electroceutical device outside the bio-electroceutical device by applying an electrical signal from an active component working electrode DC WE of an active component channel 923 to an active component counter electrode DC CE of the active component channel 923. Also, the cell controller 920 may apply an electrical stimulation to the blood vessel 991 and the capillary 992 by applying an electrical signal from a body working electrode BC WE of a body channel 924 to a body counter electrode BC CE of the body channel 924. The cell controller 920 may facilitate a deposition of an extracellular matrix (ECM) through an electrical stimulation of the active component channel 923, to increase an epidermal growth factor (EGF) and a vascular endothelial growth factor (VEGF). Thus, in response to the electrical stimulation, a curing and regenerating of the capillary 992 may result. As described above, the capillary 992 may be regenerated in response to the electrical stimulation, and accordingly the capillary 992 may grow to a position closer to the bio-electroceutical device such that a gap between the capillary 992 and a position (for example, an outer surface of a porous membrane) in which an active component is discharged from the bio-electroceutical device is reduced. Thus, a connectivity between the capillary 992 and the bio-electroceutical device may be strengthened in response to the gap being reduced. Thus, the engraftment rate of the bio-electroceutical device may be further increased in response to the connectivity being strengthened.

To facilitate the regeneration of the capillary 992 in the implantation mode as described above, the cell controller 920 may apply a DC stimulation or a low-frequency AC stimulation as an iontophoretic stimulation. A frequency of the low-frequency AC stimulation may be included in the delta frequency band 710 or the theta frequency band 720 of FIG. 7, for example.

Figure 10:
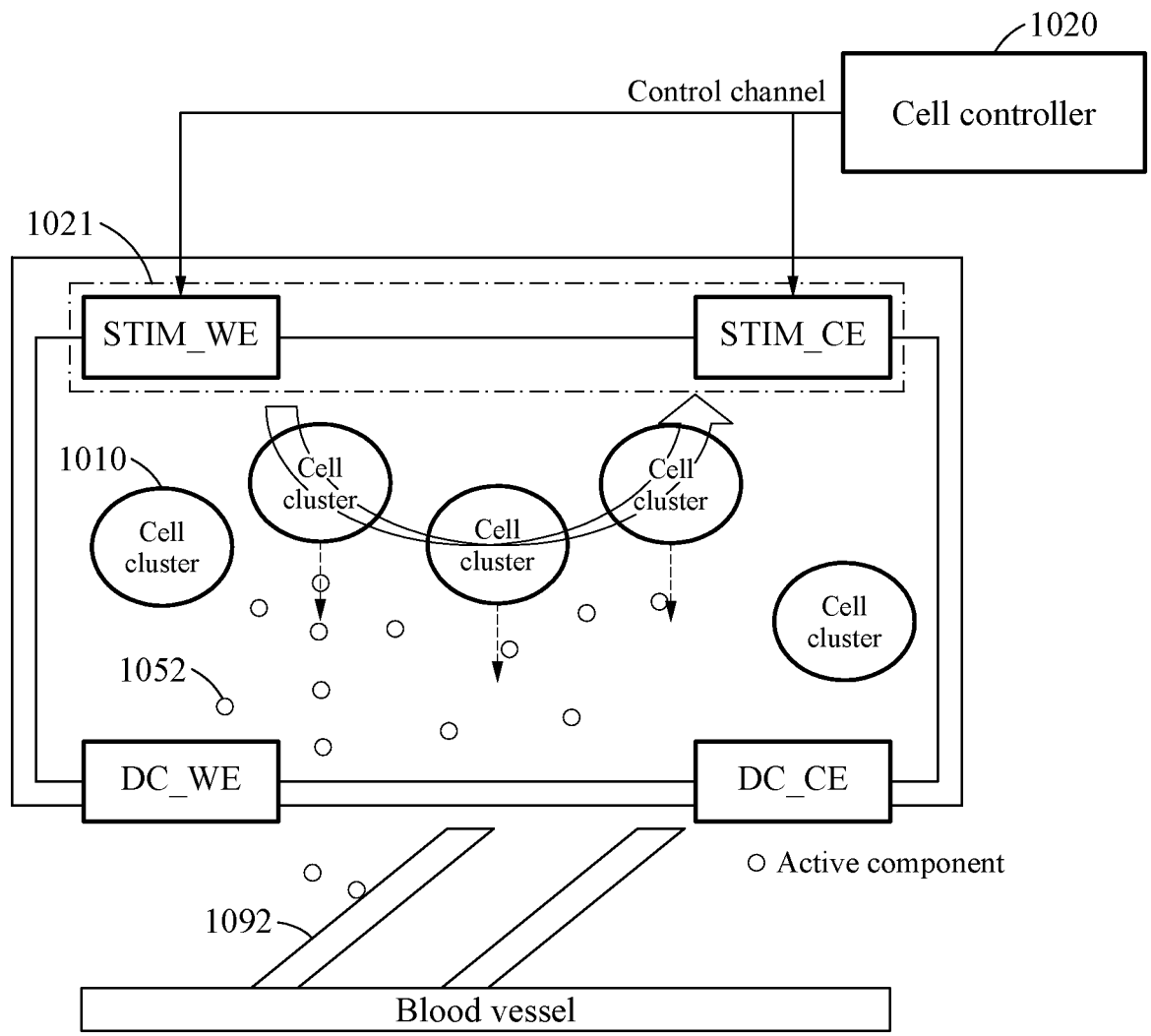
FIG. 10 illustrates an example of an operation of a bio-electroceutical device in a treatment mode.

FIG. 10 illustrates an example of a treatment operation performed by a bio-electroceutical device.

A treatment mode indicates a stage in which the bio-electroceutical device secretes an active component for a treatment. A cell controller 1020 may monitor a concentration of a target molecule in a body through a control channel and a body channel. The cell controller 1020 may provide an electrical stimulation for activating a secretion of an active component by an organoid in a cell cluster 1010 through a control channel or may terminate the electrical stimulation. The bio-electroceutical device may increase therapeutic effect by adjusting an active component generation rate based on sensed information.

In response to the bio-electroceutical device being in the treatment mode, the cell controller 1020 may facilitate the secretion of the active component by the organoid in the cell cluster 1010 by applying an electrical signal to the cell cluster 1010 through an electrode of the control channel. For example, the cell controller 1020 may apply an electrical stimulation to the cell cluster 1010 by applying an electrical signal with a predetermined frequency (e.g., any one of frequencies 710-790 shown in FIG. 7) from a stimulation working electrode STIM_WE of a stimulation channel 1021 to a stimulation counter electrode STIM_CE of the stimulation channel 1021. The organoid in the cell cluster 1010 to which the electrical stimulation is applied may secrete an active component 1052. The active component 1052 secreted by the organoid in the cell cluster 1010 may be discharged from a cell reservoir and the discharged active component 1052 may be absorbed into a capillary 1092.

As described above, the cell controller 1020 may monitor a concentration of a target molecule introduced into the cell reservoir through a sensing channel electrode and a body channel electrode and a concentration of a target molecule in a body and may provide an electrical stimulation based on a result of the monitoring, to activate the secretion of the active component by the organoid in the cell cluster 1010. Thus, the bio-electroceutical device may enhance a secretion ability of the active component 1052 by the organoid in the cell cluster 1010 through the electrical stimulation, to increase therapeutic effect. When the capillary 1092 is grown to be closer to the bio-electroceutical device as described above with reference to FIG. 9, the active component 1052 secreted by the bio-electroceutical device may be more effectively absorbed into a human body.

Figure 11:
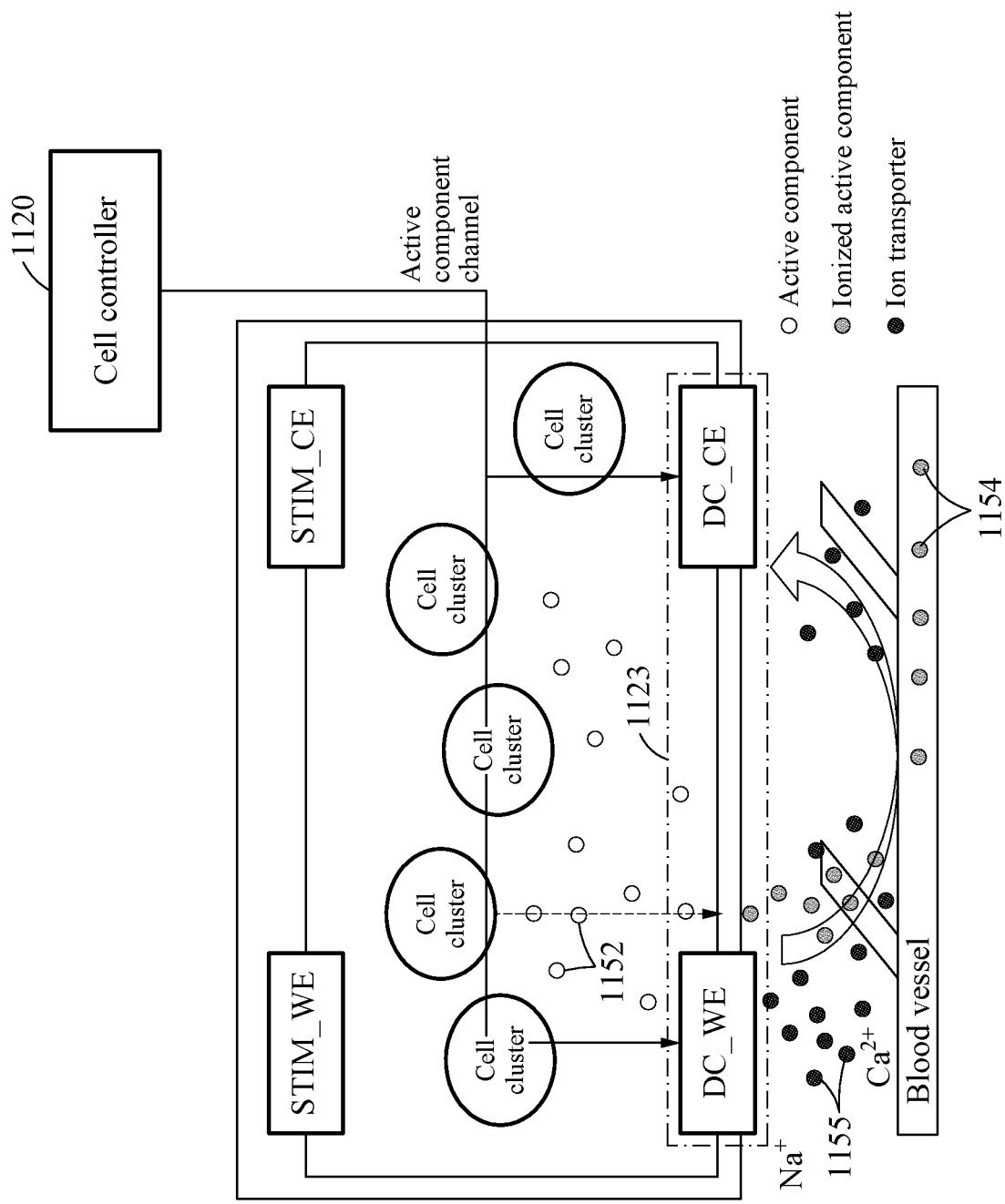
FIG. 11 illustrates an example of facilitating an absorption of an active component by a bio-electroceutical device.

FIG. 11 illustrates an example of facilitating an absorption of an active component by a bio-electroceutical device.

A cell controller 1120 may control a diffusion rate and a diffusion direction of an ionized active component 1154 by applying an electrical signal to the outside through an active component channel electrode in a treatment mode. In other words, in response to the bio-electroceutical device being in the treatment mode, the cell controller 1120 may induce a movement of an active component discharged from the bio-electroceutical device and combined with an ion transporter to a blood vessel, by applying an electrical signal through the active component channel electrode.

For example, as shown in FIG. 11, an active component 1152 discharged from the bio-electroceutical device through a porous membrane may be combined with an ion transporter 1155 adjacent to the bio-electroceutical device and may be ionized. The active component combined with the ion transporter 1155 may be referred to as the ionized active component 1154. The ion transporter 1155 may include, for example, calcium ($Ca^{2+}$) ions or sodium ($Na^+$) ions present in the body. Sodium may be combined with blood glucose and calcium may be combined with insulin.

In FIG. 11, the cell controller 1120 may apply an electrical signal through an active component channel 1123, independently of an operation of facilitating a secretion of an active component by an organoid in a cell cluster through a stimulation channel. The cell controller 1120 may form an electric path through a capillary from an electrode of the bio-electroceutical device by applying an electrical signal from an active component working electrode DC WE to an active component counter electrode DC CE. The ionized active component 1154 exhibiting polarity may be accelerated along the electric path, and accordingly the cell controller 1120 may form the electric path through the active component channel 1123 to control the diffusion direction of the ionized active component 1154. Also, the cell controller 1120 may change a magnitude of an electrical signal applied to the active component channel 1123 to control the diffusion rate of the ionized active component 1154. For example, the cell controller 1120 may increase the magnitude of the electrical signal applied to the active component channel 1123 to increase the diffusion rate of the ionized active component 1154, or the cell controller 1120 may decrease the magnitude to decrease the diffusion rate. For example, the cell controller 1120 may apply a DC electrical signal or a low-frequency AC electrical signal to the active component channel 1123 as an iontophoretic stimulation.

Thus, the bio-electroceutical device may secrete and transfer the ionized active component 1154 combined with an ion transporter using microcurrents as an additional electrical stimulation, to enhance a rate of an input of the active component 1152 into a blood vessel.

Figure 12:
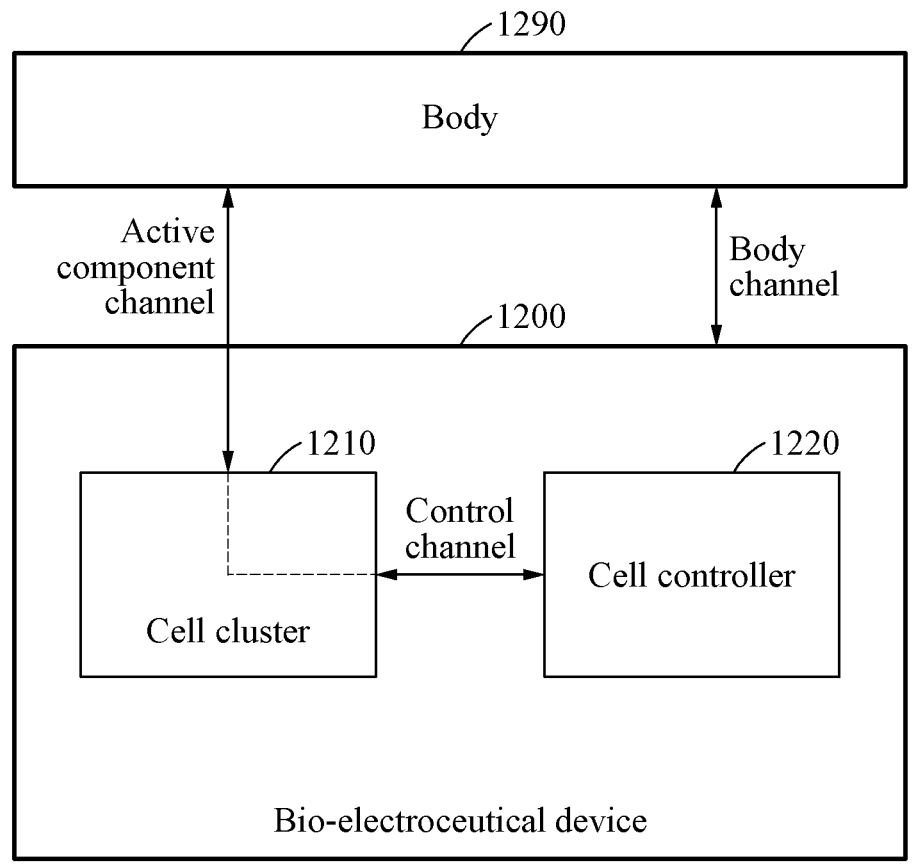
FIG. 12 illustrates an example of an integral structure of a bio-electroceutical device.

FIG. 12 illustrates an example of an integral structure of a bio-electroceutical device 1200.

The bio-electroceutical device 1200 of FIG. 12 may operate using any or all of the various channels described above with reference to FIGS. 1 through 11, and may provide an active component to a body 1290.

The bio-electroceutical device 1200 may be implemented as a system in which a cell cluster 1210 and a cell controller 1220 are integrated. For example, a porous membrane may accommodate both a cell reservoir that includes the cell cluster 1210, and the cell controller 1220. However, examples are not limited thereto, and the bio-electroceutical device 1200 may be implemented with a structure in which the cell reservoir including the cell cluster 1210 is disposed inside the porous membrane, in which the cell controller 1220 is separately packaged outside the porous membrane and in which the cell reservoir is detachable from the cell controller 1220.

Hereinafter, an example of a structure in which the porous membrane integrally accommodates the cell cluster 1210 and the cell controller 1220 will be described with reference to FIG. 13, and examples of a structure in which the cell reservoir is detachable from the cell controller 1220 will be described with reference to FIGS. 14 and 15.

FIG. 13 illustrates an example of an application of a bio-electroceutical device.

The bio-electroceutical device of FIG. 13 is a device in which a cell cluster 1310 and a cell controller 1320 are integrated. For example, a porous membrane 1330 may accommodate a cell reservoir that accommodates a cell cluster 1310, and a cell controller 1320 (e.g., as described above with reference to FIG. 4).

In response to a concentration level of a sensed target molecule being within a first range, the cell controller 1320 may apply an electrical stimulation that facilitates a secretion of an active component by an organoid in the cell cluster 1310 to the cell cluster 1310. In response to the concentration level of the sensed target molecule being within a second range, the cell controller 1320 may interrupt (e.g., cease or reduce) the electrical stimulation to the cell cluster 1310. The above-described first range and second range are different from each other. In an example, when the concentration level of the target molecule is determined to be within the first range, the bio-electroceutical device may allow the secretion of the active component by promoting the organoid in the cell cluster 1310, to adjust the concentration level of the target molecule to be in the second range. In another example, when the first range is greater than the second range, the bio-electroceutical device may lower the concentration level of the target molecule from the first range to the second range using the active component secreted by the organoid in the cell cluster 1310. However, examples are not limited thereto. In another example, when the first range is less than the second range, the bio-electroceutical device may increase the concentration level of the target molecule from the first range to the second range using the active component secreted by the organoid in the cell cluster 1310. The first range may be an abnormal range, and the second range may be a normal range.

As shown in FIG. 13, the bio-electroceutical device may sense blood glucose 1311 as a target molecule, and the organoid in the cell cluster 1310 including a beta cell organoid may secrete insulin 1312 as an active component for the blood glucose 1311.

The porous membrane 1330 may accommodate electrodes of a control channel (for example, a stimulation channel 1321 and a sensing channel 1322), in addition to the cell cluster 1310 and the cell controller 1320 described above. The porous membrane 1330 may have a structure that allows the blood glucose 1311 and oxygen to be introduced into the cell reservoir and allows the insulin 1312 to be discharged, and encloses the cell cluster 1310, the cell controller 1320, and the electrodes of the control channel. The cell cluster 1310 may be, for example, a 3D structure in which the beta cell organoid and hydrogel are fused, as shown in FIG. 13. An electrochemical sensor formed in an electrode of the sensing channel 1322 may sense a blood glucose level in a body.

In response to the sensed blood glucose level exceeding a threshold level, the cell controller 1320 may apply, to the cell cluster 1310, an electrical stimulation that facilitates a secretion of insulin by the organoid in the cell cluster 1310. Thus, the bio-electroceutical device may secrete the insulin 1312 for treatment of a diabetic patient, using the cell cluster 1310 that includes a fusion, derived from stem cells, with a secretion ability of the insulin 1312. Thus, the bio-electroceutical device may maintain the blood glucose level in the body within a normal range.

The bio-electroceutical device may have a structure in which the electrochemical sensor, the cell cluster 1310 and the cell controller 1320 are integrated as shown in FIG. 13, however, examples are not limited thereto. An example of a structure in which a cell cluster and a cell controller 1420 are separable is described below with reference to FIG. 14.

Figure 14:
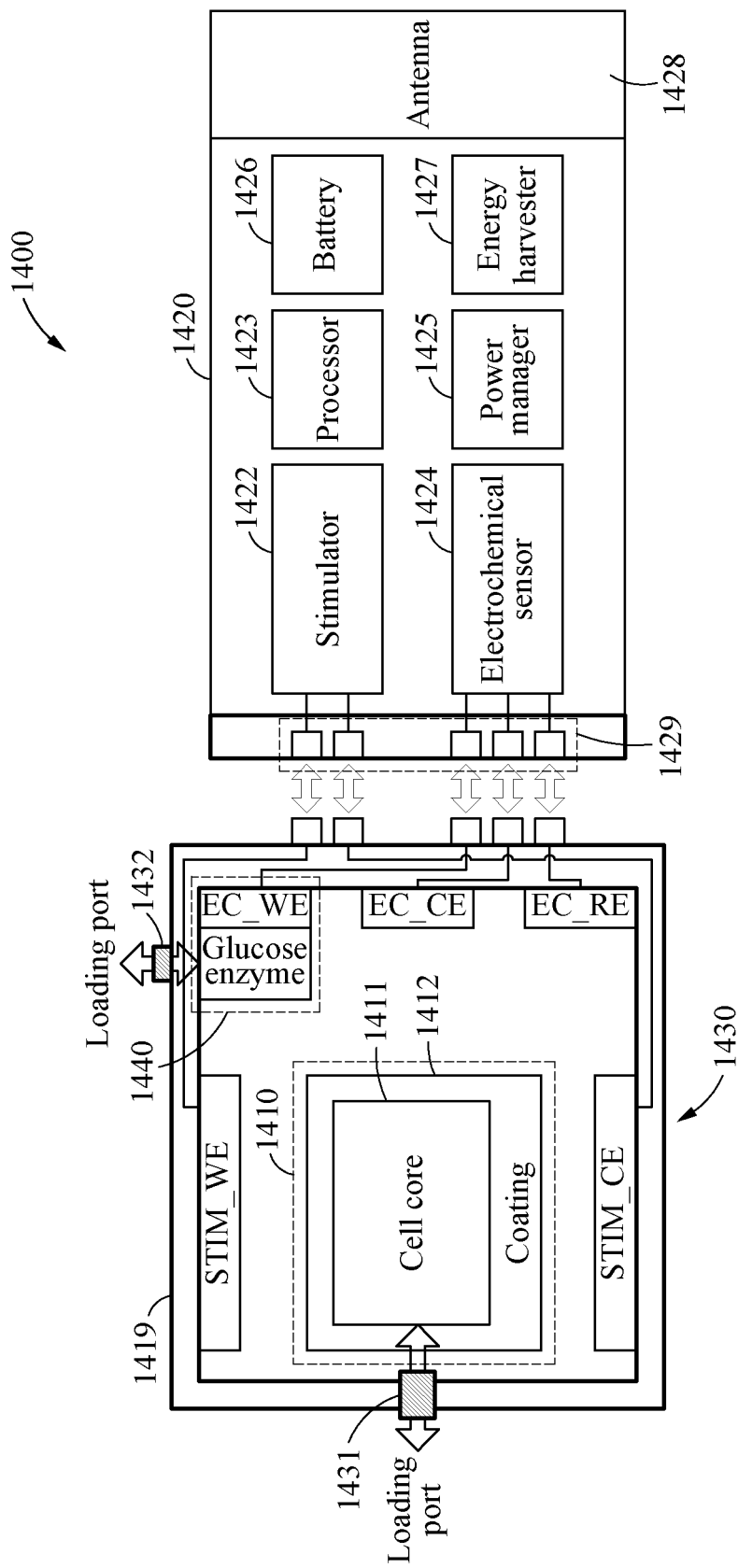
FIGS. 14 and 15 illustrate examples of structures of a cell delivery system detachable from a bio-electroceutical device.
Figure 15:
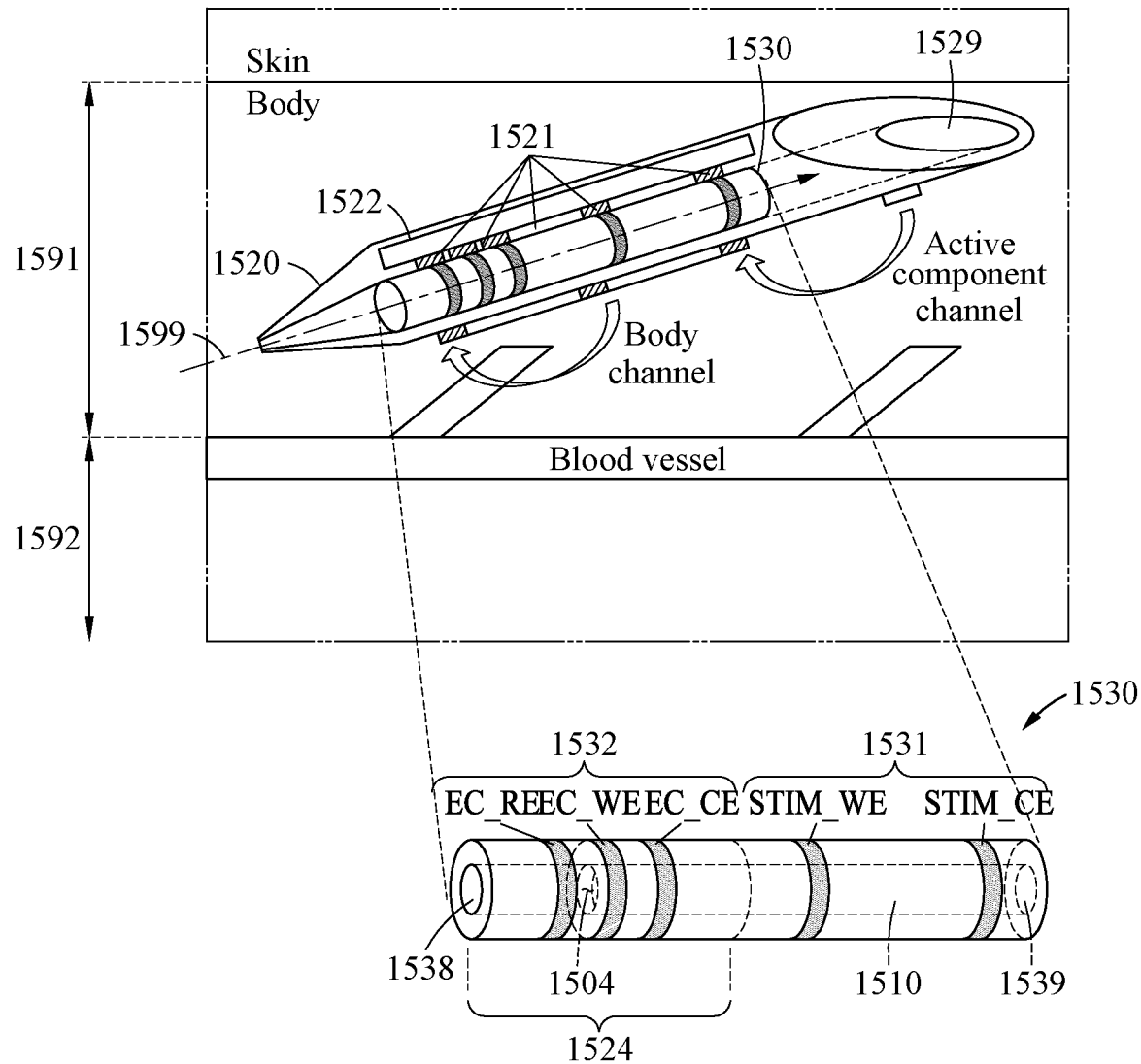

FIGS. 14 and 15 illustrate examples of structures of a cell delivery system detachable from a bio-electroceutical device.

FIG. 14 illustrates a structure in which a cell delivery system is detachable from a bio-electroceutical device 1400.

The bio-electroceutical device 1400 may include a cell controller 1420 and a cell reservoir 1430 configured to be detachable from the cell controller 1420.

The cell controller 1420 may include a stimulator 1422, a processor 1423 (e.g. one or more processors), an electrochemical sensor 1424, a power manager 1425, a battery 1426, and an energy harvester 1427 (e.g., similar to the above descriptions of FIGS. 2 and 8), and may further include an antenna 1428. The cell controller 1420 may be hermetically packaged, and each element of the cell controller 1420 may be protected from an inflow of foreign substances and liquid by the above hermetic packaging. The antenna 1428 may be exposed outside the hermetic packaging and may be configured to establish a wireless communication with an external device outside a body via a communicator (for example, either of the communicator 228 of FIG. 2 and the communicator 828 of FIG. 8) or to wirelessly receive a signal from the external device. Also, the cell controller 1420 may include a feedthrough connector 1429 corresponding to a control channel as a connector for establishing an electrical connection to the cell reservoir 1430.

The cell reservoir 1430 may accommodate a cell cluster and may be detachable from the cell controller 1420. The cell reservoir 1430 may include electrodes of an active component channel that may apply an electrical signal to a body 1490. The cell reservoir 1430 may form an electrical connection to the cell controller 1420, and an electrical signal may be applied to the electrodes of the active component channel based on a control of the cell controller 1420. The cell controller 1420 may apply an electrical signal to the body 1490 through a body channel. The cell controller 1420 and the cell reservoir 1430 may be electrically connected by an interface through the control channel. An outer edge of the cell reservoir 1430 may be packaged through a porous membrane 1419.

The cell accommodating space 1410 may be an internal space of the cell reservoir 1430 and may accommodate a cell core 1411 and a coating 1412 for the cell core 1411. For example, the cell core 1411 may be a beta pancreatic cell organoid, and the coating 1412 may be a hydrogel as a biomaterial. The cell accommodating space 1410 may accommodate at least one cell cluster in which the cell core 1411 and the coating 1412 are fused.

The cell reservoir 1430 may include electrodes corresponding to the control channel and the active component channel, together with the cell accommodating space 1410. A stimulation working electrode STIM_WE and a stimulation counter electrode STIM_CE for an electrical stimulation may be disposed inside the porous membrane 1419 of the cell reservoir 1430. Also, a sensing working electrode EC_WE, a sensing reference electrode EC_RE, and a sensing counter electrode EC CE for an electrochemical sensor may be disposed inside the porous membrane 1419. The electrodes corresponding to the control channel in the cell reservoir 1430 may be as described above with reference to FIG. 14, however, examples are not limited thereto. An electrode corresponding to the active component channel may be additionally disposed outside the cell reservoir 1430.

Also, the cell reservoir 1430 may further include an enzyme reservoir 1440. The enzyme reservoir 1440 may store an enzyme that generates an electrical signal through a chemical reaction with a target molecule. For example, when the target molecule is blood glucose, the enzyme reservoir 1440 may store a glucose oxidase enzyme (GOx). The enzyme reservoir 1440 may be disposed adjacent to an electrode (for example, a sensing working electrode EC_WE) of a sensing channel.

The cell reservoir 1430 may be configured to be replaceable. When a cell cluster is exhausted, a user may exchange the cell reservoir 1430 with a new cell reservoir.

The cell reservoir 1430 may be configured to enable a reinjection of a cell cluster. A cell cluster may include a fusion of an organoid and a biomaterial as described above, and the organoid may be protected by the biomaterial during an injection. Accordingly, the cell cluster may be injected through a loading port 1431. When a cell cluster stored in the cell reservoir 1430 is exhausted, a user may refill the cell reservoir 1430 with new cell clusters. For example, the above-described cell reservoir 1430 and enzyme reservoir 1440 may be configured to be reinjected through loading ports 1431 and 1432. The cell reservoir 1430 may include the loading port 1431 through which an additional cell cluster is injected from the outside. The cell reservoir 1430 may include the loading port 1432 through which an additional enzyme is injected from the outside.

Referring to FIG. 15, a cell reservoir 1530 detachable from a bio-electroceutical device may be configured in a form of a pod. The bio-electroceutical device may be inserted into a body part (for example, a dermal layer 1591) under a skin. The dermal layer 1591 is, for example, a layer with a thickness up to approximately 5 mm under the skin. The bio-electroceutical device may be injected between a subcutaneous layer 1592 and skin.

The cell controller 1520 may include a flow path through which a body fluid flow 1599 passes. Also, the cell controller 1520 may accommodate the cell reservoir 1530 in the flow path, and may discharge the body fluid flow 1599 flowing into the cell controller 1520 through the flow path, from the cell controller 1520 via the cell reservoir 1530. For example, the cell controller 1520 may allow a body fluid to flow therein through an inlet formed at a front end thereof, and may discharge the body fluid through an opening 1529 formed at a distal end thereof.

Also, the cell reservoir 1530 may include a housing insertable into the cell controller 1520, and is exchanged through the opening 1529. In an example, the cell reservoir 1530 mounted in the cell controller 1520 may move in a longitudinal direction of the cell controller 1520 and may be pulled out through the opening 1529 to be detached from the cell controller 1520. In another example, the cell reservoir 1530 may be inserted through the opening 1529, may move in the longitudinal direction of the cell controller 1520 and may be coupled to the cell controller 1520.

The cell reservoir 1530 may accommodate a cell cluster and an electrochemical sensor 1524 therein, and may include electrodes disposed outside the cell reservoir 1530 to be electrically connected to the cell controller 1520. For example, when the cell controller 1520 and the cell reservoir 1530 are coupled, electrode connectors 1521 of a control channel of the cell controller 1520 may be disposed to be electrically connected to stimulation channel electrodes 1531 and sensing channel electrodes 1532 of the cell reservoir 1530. A body channel electrode and an active component channel electrode are disposed outside the cell controller 1520 as shown in FIG. 15, however, examples are not limited thereto.

The electrochemical sensor 1524 may be formed in the cell reservoir 1530. For example, the cell reservoir 1530 may include an inlet 1538 through which fluid flows into the cell reservoir 1530, an outlet 1539 through which fluid is discharged, and a flow path formed between the inlet 1538 and the outlet 1539. Porous membranes may be disposed in the inlet 1538 and the outlet 1539. The flow path may be defined by an inner surface 1504 of the cell reservoir 1530. An enzyme capable of reacting with a target molecule (for example, a blood glucose) may be applied onto the inner surface 1504 of the cell reservoir 1530. The applied enzyme may be electrically connected to a sensing working electrode exposed outside the cell reservoir 1530. Thus, a target molecule introduced into the cell reservoir 1530 through the flow path may react with the enzyme.

Also, the cell reservoir 1530 may accommodate a cell cluster in a portion of a space (for example, a cell accommodation space 1510) of the flow path. A sensing working electrode 1531 exposed outside the cell reservoir 1530 may be connected to the cell accommodation space 1510 in the cell reservoir 1530. An organoid in the cell cluster may secrete an active component based on an electrical stimulation determined by a processor 1522 (e.g., one or more processors) of the cell controller 1520. The active component secreted by the organoid in the cell cluster may be discharged through the outlet 1539.

Although the cell reservoir 1530 is in a form of a cylinder as shown in FIG. 15, this is merely an example, and shapes of the cell reservoir 1530 and the cell controller 1520 are not limited thereto.

Figure 16:
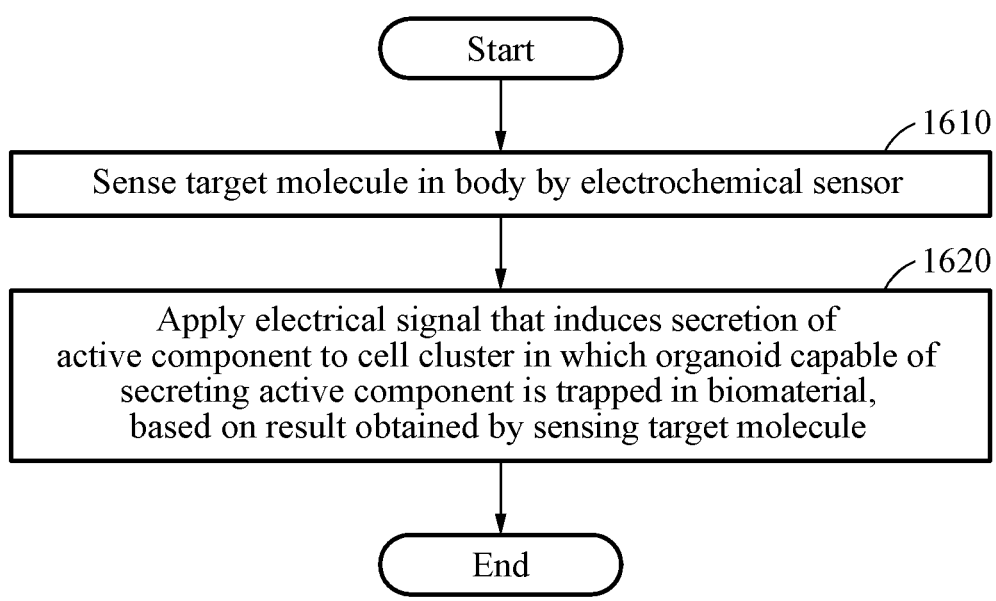
FIG. 16 illustrates an example of an active component secretion method using a bio-electroceutical device.

FIG. 16 illustrates an example of an active component secretion method using a bio-electroceutical device.

A method of controlling bio-electroceuticals inserted into a body is described. For example, a bio-electroceutical device may include an electrochemical sensor, a cell reservoir, and a cell controller.

Referring to FIG. 16, in operation 1610, the electrochemical sensor may sense a target molecule in a body. For example, the bio-electroceutical device may electrochemically sense a blood glucose concentration in the body.

In operation 1620, the bio-electroceutical device may apply an electrical signal that induces a secretion of an active component to a cell cluster in which an organoid capable of secreting the active component is trapped in a biomaterial, based on a result obtained by sensing the target molecule.

According to examples, a bio-electroceutical device may increase an engraftment rate by applying an electrical stimulation based on a cell state, and may enhance an active component secretion ability (for example, an insulin secretion ability). Also, the bio-electroceutical device may exhibit a high blood glucose detection ability using an electrochemical sensor. Thus, the bio-electroceutical device may accurately secrete and provide a required amount of active components based on a state of a body.

However, the active component secretion method of FIG. 16 is not limited thereto, and may be performed in parallel or sequentially with at least one of the operations described above with reference to FIGS. 1 through 15.

The bio-electroceutical devices, cell controllers, channel switches, stimulators, processors, electrochemical sensors, power managers, batteries, energy harvesters, communicators, controllers, cell controllers, stimulation channels, sensing channels, active component channels, body channels, antennas, feedthrough connectors, electrodes, bio-electroceutical device 100, cell controller 120, bio-electroceutical device 200, cell controller 220, channel switch 221, stimulator 222, processor 223, electrochemical sensor 224, power manager 225, battery 226, energy harvester 227, communicator 228, controller 320, cell controller 420, stimulation channel 422, sensing channel 421, electrochemical sensors 510, 520, and 530, cell controller 820, channel switch 821, stimulator 822, processor 823, electrochemical sensor 824, power manager 825, battery 826, energy harvester 827, communicator 828, cell controller 920, active component channel 923, body channel 924, cell controller 1020, stimulation channel 1021, cell controller 1120, active component channel 1123, bio-electroceutical device 1200, cell controller 1220, cell controller 1320, stimulation channel 1321, sensing channel 1322, bio-electroceutical device 1400, cell controller 1420, stimulator 1422, processor 1423, electrochemical sensor 1424, power manager 1425, battery 1426, energy harvester 1427, antenna 1428, feedthrough connector 1429, cell controller 1520, electrochemical sensor 1524, stimulation channel electrodes 1531, sensing channel electrodes 1532, apparatuses, units, modules, devices, and other components described herein with respect to FIGS. 1-16 are implemented by hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-16 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions used herein, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A bio-electroceutical device comprising:
a cell reservoir with an electrode disposed within the cell reservoir and a cell cluster comprising an organoid fused with a biomaterial disposed within the cell reservoir; and
a cell controller configured to control, using an electrical signal applied by the electrode, a secretion of an active component by the organoid in the cell cluster.

2. The device of claim 1, wherein the cell cluster is accommodated in the cell reservoir, the biomaterial comprises a hydrogel, the organoid comprises a beta cell organoid, and the cell cluster comprises the hydrogel and the beta cell organoid disposed in the hydrogel.

3. The device of claim 1, further comprising:
an electrochemical sensor configured to sense a target molecule,
wherein, for the control of the secretion, the cell controller is configured to adjust an active component generation rate of the organoid in the cell cluster based on a result of the sensing of the target molecule by the electrochemical sensor.

4. The device of claim 3, wherein, to sense the target molecule, the electrochemical sensor is configured to sense another electrical signal generated by a reaction between the target molecule and an enzyme.

5. The device of claim 3, wherein, for the control of the secretion, the cell controller is configured to perform either one or both of:
applying an electrical stimulation that facilitates the secretion of the active component by the organoid in the cell cluster; and
interrupting the electrical stimulation based on a concentration of the sensed target molecule.

6. The device of claim 5, wherein the interrupting of the electrical stimulation comprises either one or both of reduction of a level of the electrical stimulation and termination of the application of the electrical stimulation.

7. The device of claim 3, wherein, for the control of the secretion, the cell controller is configured to:
identify a metabolic state of a body based on a concentration of the sensed target molecule; and
determine whether to apply an electrical stimulation to the cell cluster based on the identified metabolic state.

8. The device of claim 7, wherein:
to sense the target molecule, the electrochemical sensor is configured to sense a changed concentration of the target molecule, in response to the active component being secreted by the organoid in the cell cluster with the adjusted active component generation rate based on the electrical stimulation, and
for the control of the secretion, the cell controller is configured to reidentify the metabolic state based on the changed concentration and to redetermine whether to apply the electrical stimulation to the cell cluster based on the reidentified metabolic state.

9. The device of claim 3, wherein, for the control of the secretion, the cell controller is configured to:
apply, to the cell cluster, an electrical stimulation that facilitates the secretion of the active component by the organoid in the cell cluster, in response to a concentration level of the sensed target molecule being within a first range; and
interrupt the electrical stimulation to the cell cluster, in response to the concentration level of the sensed target molecule being within a second range.

10. The device of claim 3, wherein:
the active component comprises insulin and the target molecule comprises blood glucose,
the electrochemical sensor is configured to sense a blood glucose level of a body, and
for the control of the secretion, the cell controller is configured to apply, to the cell cluster, an electrical stimulation that facilitates a secretion of the insulin by the organoid in the cell cluster, in response to the sensed blood glucose level exceeding a threshold level.

11. The device of claim 3, wherein, for the control of the secretion, the cell controller is configured to:
determine a target generation rate for the active component generation rate based on the result of sensing the target molecule by the electrochemical sensor; and
determine any one or any combination of a pulse width, a magnitude, a frequency, a phase and a waveform of the electrical signal, wherein the electrical signal is applied to the cell cluster based on the determined target generation rate.

12. The device of claim 3, wherein, for the control of the secretion, the cell controller is configured to:
determine a frequency of the electrical signal to be within any one of a beta frequency band, a gamma frequency band including 40 hertz (Hz), and a spike frequency band exceeding 400 Hz, and
apply the electrical signal to the cell cluster.

13. The device of claim 1, further comprising:
the electrode being a control channel electrode configured to apply the electrical signal to the cell cluster;
an active component channel electrode disposed between the cell cluster and a blood vessel; and
a body channel electrode configured to apply another electrical signal to the blood vessel.

14. The device of claim 1, wherein the cell controller is configured to facilitate a regeneration of a capillary adjacent to the bio-electroceutical device using an active component channel electrode and a body channel electrode, in response to the bio-electroceutical device being in an implantation mode.

15. The device of claim 1, wherein, for the control of the secretion, the cell controller is configured to facilitate the secretion of the active component by the organoid in the cell cluster by applying the electrical signal to the cell cluster using a control channel electrode, in response to the bio-electroceutical device being in a treatment mode.

16. The device of claim 1, wherein
the active component is discharged to an outside of the bio-electroceutical device and combined with an ion transporter, and
the cell controller is configured to induce a movement of the active component to a blood vessel by applying another electrical signal to the outside of the bio-electroceutical device using an active component channel electrode, in response to the bio-electroceutical device being in a treatment mode.

17. The device of claim 16, wherein, to apply the another electrical signal to the outside of the bio-electroceutical device, the cell controller is configured to form an electric path between the blood vessel and the active component channel electrode by applying either one of a direct current (DC) stimulation and an alternating current (AC) stimulation to the active component channel electrode.

18. The device of claim 1, wherein the cell reservoir is configured to be detached from the cell controller.

19. The device of claim 18, wherein the cell reservoir comprises a loading port configured to receive an injection of an additional cell cluster from an outside of the bio-electroceutical device.

20. A bio-electroceutical device comprising:
an electrochemical sensor configured to sense a target molecule in a body;
a cell reservoir with an electrode disposed within the cell reservoir and a cell cluster comprising an organoid fused with a biomaterial disposed within the cell reservoir; and
a cell controller configured to apply, to the cell cluster, an electrical signal applied by the electrode that induces a secretion of an active component by the organoid, based on a result of the sensing of the target molecule by the electrochemical sensor.

21. A processor-implemented method of a bio-electroceutical device, the method comprising:
sensing, using an electrochemical sensor, a concentration level of a target molecule disposed in a cell reservoir, the cell reservoir with an electrode disposed within the cell reservoir;
determining a target generation rate of an active component secreted by an organoid disposed in the cell reservoir, based on the concentration level of the target molecule;
determining an electrical signal to be applied to the organoid based on the target generation rate of the active component; and
applying, using the electrode, the electrical signal to the organoid to induce the secretion of the active component at the target generation rate of the active component.

22. A non-transitory computer-readable storage medium storing instructions that, when executed by a processor, configure the processor to perform the method of claim 21.

* * * * *